US011446053B2

(12) United States Patent
Jamous et al.

(10) Patent No.: US 11,446,053 B2
(45) Date of Patent: Sep. 20, 2022

(54) TISSUE-REMOVING CATHETER INCLUDING TURBINE

(71) Applicant: MEDTRONIC VASCULAR, INC., Santa Rosa, CA (US)

(72) Inventors: Aram Jamous, Athenry (IE); John Kelly, Galway (IE); Colin William Meade, Westmeath (IE); Micheal Moriarty, Galway (IE); Barry O'Connell, Galway (IE); Grainne Carroll, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 134 days.

(21) Appl. No.: 16/794,545

(22) Filed: Feb. 19, 2020

(65) Prior Publication Data

US 2020/0261112 A1    Aug. 20, 2020

Related U.S. Application Data

(60) Provisional application No. 62/808,088, filed on Feb. 20, 2019.

(51) Int. Cl.
*A61B 17/3207* (2006.01)
*A61M 25/09* (2006.01)
(Continued)

(52) U.S. Cl.
CPC ..... *A61B 17/320758* (2013.01); *A61M 25/09* (2013.01); *A61B 2017/22001* (2013.01);
(Continued)

(58) Field of Classification Search
CPC .... A61B 17/320758; A61B 17/320725; A61B 17/320783; A61B 17/3207;
(Continued)

(56) References Cited

U.S. PATENT DOCUMENTS 4,631,052 A * 12/1986 Kensey .......... A61B 17/320758
604/22
4,895,560 A    1/1990 Papantonakos
(Continued)

FOREIGN PATENT DOCUMENTS

| CN | 205866805 U | 1/2017 |
|---|---|---|
| DE | 29521096 U1 | 8/1996 |

(Continued)

OTHER PUBLICATIONS

International Search Report and Written Opinion for PCT/US2020/018783, dated Apr. 29, 2020, 12 pages, Rijswijk, Netherlands.

*Primary Examiner* — Tuan V Nguyen
(74) *Attorney, Agent, or Firm* — Stinson LLP

(57) ABSTRACT

A tissue-removing catheter for removing tissue in a body lumen includes an elongate body having an axis and proximal and distal end portions spaced apart from one another along the axis. A turbine is fixed to the elongate body and is disposed at an intermediate position between the proximal and distal end portions of the elongate body. A rotatable tissue-removing element is at the distal end portion of the elongate body and is operatively coupled to the turbine such that the turbine imparts rotation of the tissue-removing element. The tissue-removing element removes the tissue from the body lumen as the tissue-removing element is rotated by the turbine.

21 Claims, 20 Drawing Sheets

(51) Int. Cl.
*A61B 17/22* (2006.01)
*A61B 17/32* (2006.01)

(52) U.S. Cl.
CPC ............. *A61B 2017/320004* (2013.01); *A61B 2017/320775* (2013.01)

(58) Field of Classification Search
CPC . A61B 17/32037; A61B 2017/320775; A61M 25/09
See application file for complete search history.

(56) References Cited

U.S. PATENT DOCUMENTS

| | | | |
|---|---|---|---|
| 5,195,956 A * | 3/1993 | Stockmeier | A61B 17/320758 604/22 |
| 5,314,407 A | 5/1994 | Auth et al. | |
| 5,569,275 A | 10/1996 | Kotula et al. | |
| 5,667,490 A * | 9/1997 | Keith | A61B 17/3207 173/220 |
| 5,779,721 A | 7/1998 | Nash | |
| 2002/0029057 A1 | 3/2002 | McGuckin, Jr. | |
| 2003/0144656 A1 * | 7/2003 | Ocel | A61B 5/283 606/41 |
| 2014/0024945 A1 * | 1/2014 | Mung | A61B 8/0841 600/461 |
| 2015/0018711 A1 * | 1/2015 | Furlong | A61B 1/00094 600/565 |
| 2018/0042640 A1 * | 2/2018 | Govari | F01D 1/06 |

FOREIGN PATENT DOCUMENTS

| | | |
|---|---|---|
| NL | 1016653 C2 | 5/2002 |
| WO | 2016/011312 A1 | 1/2016 |

\* cited by examiner 154
156
158

TISSUE-REMOVING CATHETER INCLUDING TURBINE

CROSS-REFERENCE TO RELATED APPLICATIONS

This application claims priority to U.S. Provisional Application No. 62/808,088, filed Feb. 20, 2019, the entirety of which is hereby incorporated by reference.

FIELD

The present disclosure relates to tissue-removing catheters, and more particularly, to turbines that rotate the tissue-removing element of the tissue-removing catheters.

BACKGROUND

Tissue-removing catheters are used to remove unwanted tissue in body lumens. As an example, atherectomy catheters are used to remove material from a blood vessel to open the blood vessel and improve blood flow through the vessel. Some atherectomy catheters employ a rotating element which is used to abrade or otherwise break up the unwanted tissue.

SUMMARY

In one aspect, a tissue-removing catheter for removing tissue in a body lumen includes an elongate body having an axis and proximal and distal end portions spaced apart from one another along the axis. The elongate body is sized and shaped to be received in the body lumen. A turbine is fixed to the elongate body and disposed at an intermediate position between the proximal and distal end portions of the elongate body. A tissue-removing element is mounted on the distal end portion of the elongate body and is operatively coupled to the turbine. The tissue-removing element is configured to remove the tissue from the body lumen as the tissue-removing element is rotated about the axis by the turbine.

In another aspect, a method of removing tissue in a body lumen includes advancing an elongate body through the body lumen to position a distal end portion of the elongate body adjacent the tissue and a proximal end portion of the elongate body outside of the body lumen. An actuator outside the body lumen delivers a flow of propellant to a turbine mounted at an intermediate position between the proximal and distal end portions of the elongate body to rotate a tissue-removing element about a longitudinal axis of the elongate body to remove the tissue. The actuator outside the body lumen controls the flow of the propellant to the turbine to control the rotational speed and/or torque of the tissue-removing element.

Other objects and features of the present disclosure will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
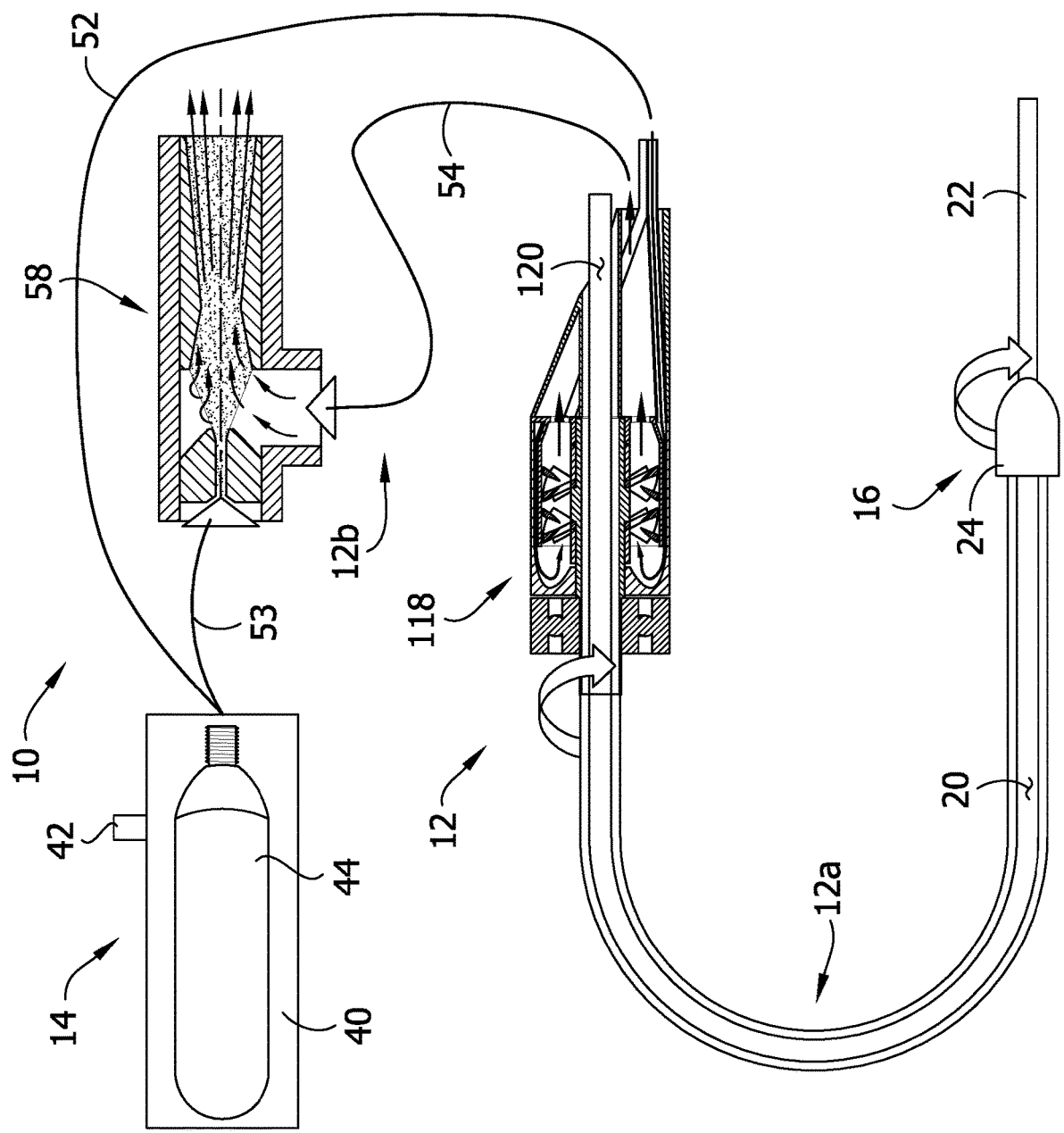
FIG. 1 is a schematic illustration of a catheter including a cross section of one embodiment of a turbine of the present disclosure.

Referring to the drawings, and in particular FIG. 1, a rotational tissue-removing catheter for removing tissue in a body lumen is generally indicated at reference number 10. The illustrated catheter 10 is a rotational atherectomy device suitable for removing (e.g., abrading, cutting, excising, ablating, etc.) occlusive tissue (e.g., embolic tissue, plaque tissue, atheroma, thrombolytic tissue, stenotic tissue, hyperplastic tissue, neoplastic tissue, etc.) from a vessel wall (e.g., coronary arterial wall, etc.). The catheter 10 may be used to facilitate percutaneous coronary angioplasty (PTCA) or the subsequent delivery of a stent. Features of the disclosed embodiments may also be suitable for treating chronic total occlusion (CTO) of blood vessels, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen.

The catheter 10 is sized for being received in a blood vessel of a subject. Thus, the catheter 10 may have a maximum size of 3, 4, 5, 6, 7, 8, 9, 10, or 12 French (1, 1.3, 1.7, 2, 2.3, 2.7, 3, 3.3, or 4 mm) and may have a working length of 20, 30, 40, 60, 80, 100, 120, 150, 180 or 210 cm depending of the body lumen. While the remaining discussion is directed toward a catheter for removing tissue in blood vessels, it will be appreciated that the teachings of the present disclosure also apply to other types of tissue-removing catheters, including, but not limited to, catheters for penetrating and/or removing tissue from a variety of occlusive, stenotic, or hyperplastic material in a variety of body lumens.

Referring to FIGS. 1-3 and 14, the catheter 10 comprises an elongate body 12 having a longitudinal axis LA and proximal and distal end portions 14 and 16, respectively, spaced apart along the axis. The catheter 10 includes one embodiment of a turbine, generally indicated at 118. In the illustrated embodiment, the turbine is disposed at an intermediate position along the catheter body 12. In this embodiment, the turbine 118 divides the elongate body 12 into a distal portion (e.g., distal body portion) 12a that extends distally from the turbine to the distal end portion 16 of the catheter 10 and a proximal portion (e.g., proximal body portion) 12b that extends proximally from the turbine to the proximal end portion of the catheter. The distal body portion 12a is sized and shaped for insertion into a body lumen of a subject. The turbine 118 may also be sized and shaped for insertion into the body lumen. The distal body portion 12a defines a guidewire lumen 20 for slidably receiving a guidewire 22 therein so that the catheter 10 can be advanced through the body lumen by traveling along the guidewire. The guidewire lumen 20 extends distally from the turbine 118 to the distal end portion 16 of the catheter 10. In certain embodiments, the distal body portion 12a may have a lubricious inner surface for sliding over the guidewire 22 (e.g., a lubricious surface may be provided by a lubricious polymer layer or a lubricious coating). A tissue removing element 24 is disposed at the distal end of the distal body portion 12a and is configured for rotation to remove tissue from a body lumen. The tissue removing element 24 is operatively connected to the turbine 118, such as by a drive shaft 26 as explained in more detail below, for being selectively rotated by the turbine about the longitudinal axis LA of the catheter 10. In one example, the guidewire lumen 20 extends longitudinally through the drive shaft 26. When the distal body portion 12a of the catheter 10 is inserted into the body lumen and the turbine 118 rotates the tissue removing element 24, the tissue removing element removes occlusive tissue in the body lumen by separating the occlusive tissue from the wall of the body lumen.

Figure 2:
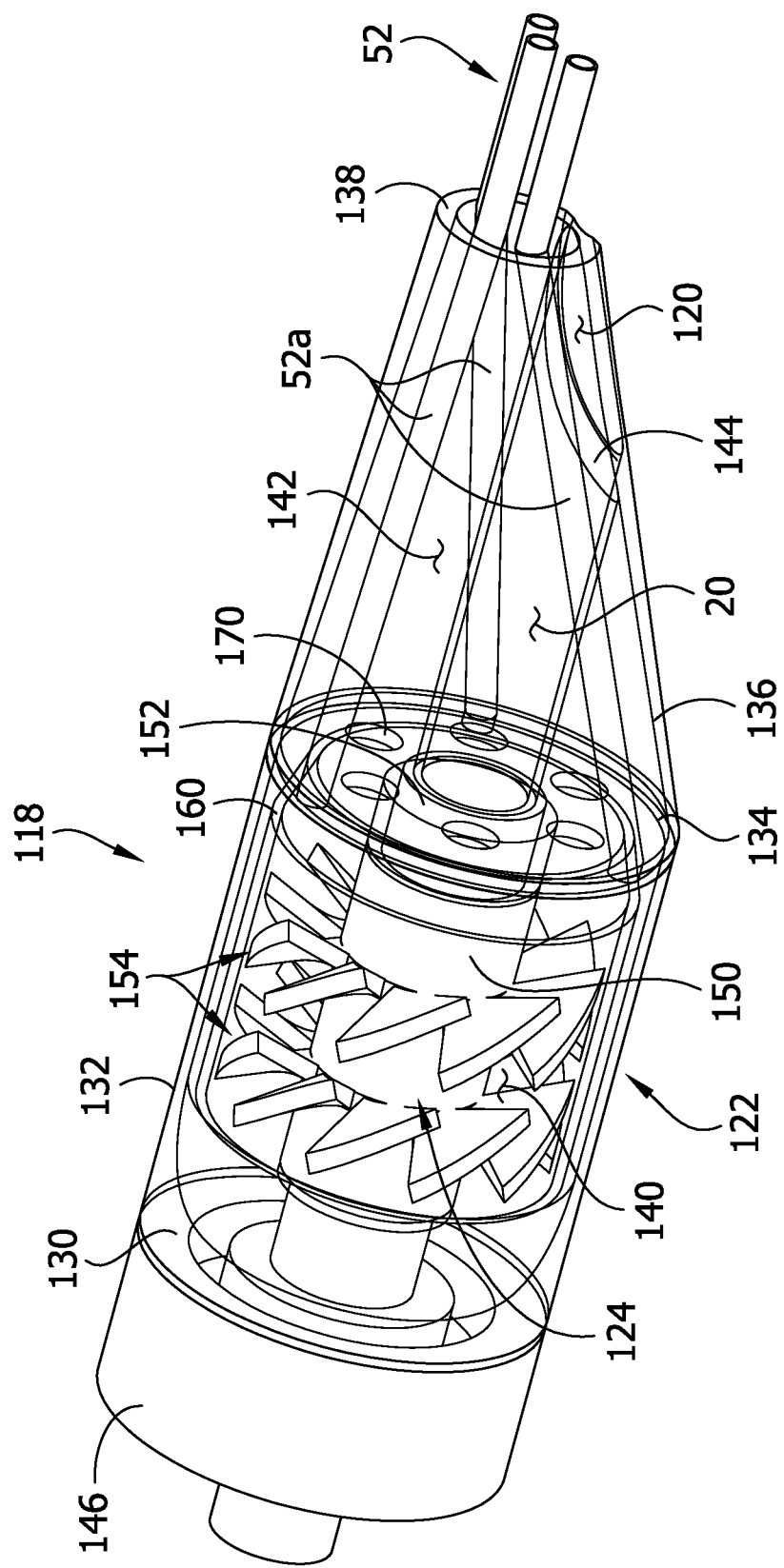
FIG. 2 is a perspective of the turbine of FIG. 1, with portions thereof being transparent to show internal components.

Referring to FIGS. 1 and 2, the turbine 118 defines a guidewire port 120 which may also define a portion of the guidewire lumen 20 (e.g., the guidewire port may define a proximal end of the guidewire lumen). The guidewire port 120 provides an exit location for the guidewire 22 at an intermediate location on the catheter 10. The guidewire 22 can be a standard 0.014 inch (0.4 mm) outer diameter guidewire. The illustrated turbine 118 allows for a shorter guidewire 22 to be used with the catheter 10 because the guidewire exits the catheter at the intermediate location on the catheter rather than extending along the entire working length of the catheter. In one embodiment, a guidewire 22 having a length of less than about 200 cm (about 79 inches) may be used with the catheter 10. In one embodiment, a guidewire 22 having a length of between about 150 cm (59 inches) and about 190 cm (75 inches) can be used. In the illustrated embodiment, the guidewire lumen 20 extends from the turbine 118 through the distal end portion 16 of the catheter 10 such that the guidewire 22 is extendable along only a portion of the working length of the catheter 10. In one embodiment, the overall working length of the catheter 10 may be between about 135 cm (53 inches) and about 142 cm (56 inches). In use, the guidewire 22 may extend about 40 mm (1.6 inches) past the guidewire portion 120.

Figure 14:
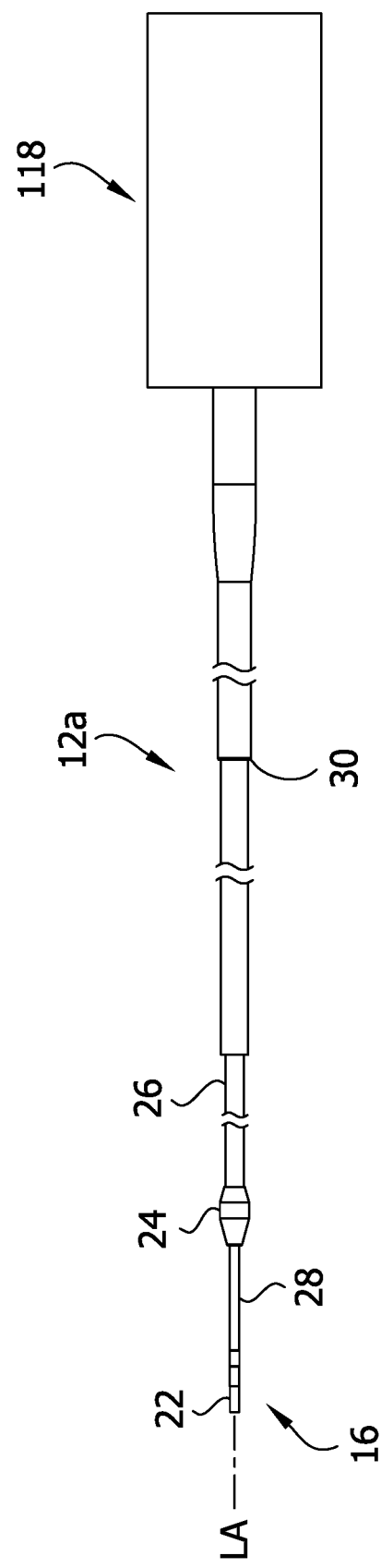
FIG. 14 is an elevation of one embodiment of a distal portion of a catheter of the present disclosure.

Referring to FIG. 14, the distal body portion 12a of the illustrated catheter 10 comprises an elongate inner liner 28, drive shaft 26, and a sheath 30. The inner liner 28 at least partially defines the guidewire lumen 20 extending through the drive shaft 26. The drive shaft 26 is configured to rotate about the inner liner 28, although the inner liner may rotate with the drive shaft. The sheath 30 is disposed around the drive shaft 26 and isolates the body lumen from at least a portion of the drive shaft 26 and inner liner 28. The sheath 30, the drive shaft 26, and the inner liner 28 extend distally from the turbine 118. As explained in more detail below, rotation of the drive shaft 26 by the turbine 118 rotates the tissue removing element 24. In the illustrated embodiment, the tissue removing element 24 comprises an abrasive burr. In other embodiments, the tissue removing element may comprise a rotatable cutter (e.g., a cutter with an annular cutter edge) or other types of tissue removing elements.

Referring to FIGS. 1-4, the first embodiment of the turbine 118 includes a housing, generally indicated at 122 (e.g., stator), enclosing a rotor 124 configured to rotate within the housing. The rotor 124 is operatively connected to the tissue removing element 24 such that rotation of the rotor in the housing 122 drives rotation of the tissue removing element. In one embodiment, the turbine 118 is configured to rotate the tissue removing element 24 at speeds of greater than about 80,000 RPM while generating a torque of about 1.5 mNm. In one embodiment, the turbine 118 is a micro-turbine that is sized and arranged for being received in the body lumen of the subject. In one embodiment, the turbine 118 has an outer diameter from about 0.5 mm to about 4 mm. The turbine 118 is sized such that it can be received within a guide catheter (not shown). In one embodiment, the turbine 118 is sized so that the catheter 10 can be received in a 7 F (about 2 mm) or smaller diameter guide catheter. In another embodiment, the turbine 118 is sized so that the catheter 10 can be received in a 6 F (about 1.8 mm) or smaller diameter guide catheter. The turbine 118 is cannulated such that the turbine is a through-hole turbine. In this manner, the turbine 118 defines a portion of the guidewire lumen 20 that extends along a drive axis DA (FIG. 3) of the turbine. The portion of the guidewire lumen 20 defined by the turbine 118 is aligned with the portion of the guidewire lumen defined by the inner liner 28 of the distal body portion 12a (e.g., the drive axis DA is coaxial with the longitudinal axis LA of the catheter 10) so that the guidewire 22 may extend from the distal body portion into the turbine or vice versa without bending, curving, or changing direction (FIG. 1).

Figure 3:
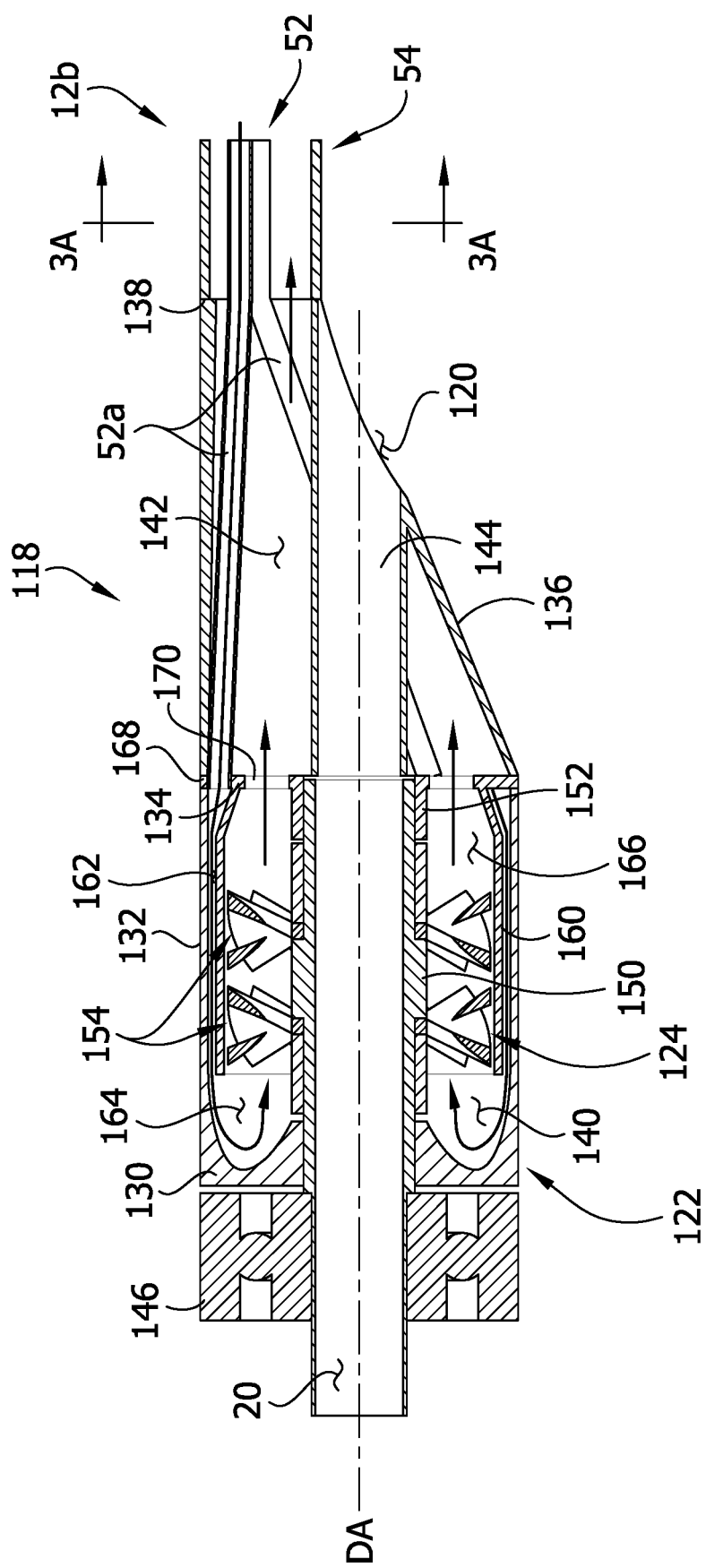
FIG. 3 is a cross section taken longitudinally through the turbine of FIG. 2.

Referring to FIGS. 2 and 3, the housing 122 includes a distal end wall 130, an outer cylindrical wall 132 extending proximally from the distal end wall, a divider wall 134 at the proximal end of the outer wall and a conical wall 136 extending proximally from the proximal end of the outer wall to a tip 138 of the conical wall. The outer wall 132 defines a rotor chamber 140 where the rotor 124 is disposed and rotates. The conical wall 136 defines an outlet chamber 142 where, as discussed in more detail below, the propellant (e.g., compressed gas) enters after the propellant moves through the rotor chamber 140. The divider wall 134 separates the rotor chamber 140 and the outlet chamber 142. The conical wall 136 defines the guidewire port 120. A cylindrical lumen wall 144, aligned with the drive axis DA, extends proximally through the outlet chamber 142 from the divider wall 134 to the guidewire port 120 on the conical wall 136 and defines a portion of the guidewire lumen 20. The divider wall 134 defines a central opening, aligned with the drive axis DA, to allow the guidewire 22 to extend through the divider wall between the rotor and outlet chambers 140, 142. The turbine 118 includes a bearing 146 mounted on the distal side of the distal end wall 130 and aligned with the drive axis DA. The bearing 146 is preferably sized such that the outer diameter of the bearing aligns with (e.g., is the same as) the outer diameter of the outer wall 132. In one embodiment, the bearing 146 has a size of 2 mm.

The housing 122 includes an intermediate cylindrical wall 160 extending distally into the rotor chamber 140 from divider wall 134 to a distal end that is proximally spaced apart from the distal end wall 130. The intermediate cylindrical wall 160 divides the rotor chamber 140 into generally three sections: an outer passageway 162, a transition section 164 and an inner passageway 166. The intermediate wall 160 is adjacent to but disposed radially inward of the outer wall 132. Together, the outer wall 132 and the intermediate wall 160 define the narrow outer passageway 162. As explained in more detail below, the propellant (as indicated by the red arrow in FIG. 3) enters the rotor chamber 140 via the outer passageway 162 and flows distally through the outer passageway to the transition section 164. The transition section 164 is defined by the distal end wall 130 and the distal end of the intermediate wall 160. As explained in more detail below, the transition section 164 is configured to redirect the flow of the propellant (as indicated by the red arrow in FIG. 3) from the outer passageway 162 into the inner passageway 166. As shown in FIG. 3, the distal end wall 130 has a generally U-shaped proximal surface in cross section that redirects the flow of the propellant from the distal direction to the proximal direction and into the inner passageway 166. In other words, the distal end wall 130 defines an annular U-shaped groove in the rotor chamber 140 and circumferentially surrounding a portion of the rotor 124. The intermediate wall 160 and rotor 124 define the inner passageway 166. As explained in more detail below, as the propellant (as indicated by the blue arrows in FIG. 3) flows proximally through the inner passageway 166 and into the outlet chamber 142, the propellant rotates the rotor 124. The divider wall 134 defines at least one (preferably, a plurality of) inlet opening 168 configured to permit the propellant to flow into the outer passageway 162 and at least one (preferably, a plurality of) outlet opening 170 configured to permit the propellant to flow out of the inner passageway 166 and into the outlet chamber 142.

The rotor 124 is disposed in the rotor chamber 140 and is configured to rotate therein. The rotor 124 includes a cylindrical drive shaft 150 extending distally through the rotor chamber 140 from the divider wall 134 through the distal end wall 130 and to the bearing 146. In one embodiment, the drive shaft extends distally through the bearing 146. The drive shaft 150 is aligned with the drive axis DA and defines a portion of the guidewire lumen 20 (e.g., the drive shaft has a bore there-through). The cylindrical drive shaft 150 has an intermediate portion with a first diameter and proximal and distal end portions with a second diameter, the second diameter being smaller than the first diameter. The proximal end portion of the drive shaft 150 is rotatably disposed in (e.g., supported by) a cylindrical bearing wall 152 that extends distally from the divider wall 134. The inner diameter of the bear wall 152 is larger than the outer diameter of the proximal end portion of the drive shaft 150 such that the drive shaft can rotate therein (e.g., a clearance is provided allowing the drive shaft to rotate about the drive axis DA in the bearing wall). Preferably, the outer diameter of the bearing wall 152 is the same as the outer diameter of the intermediate portion of the drive shaft 150. The distal end portion of the drive shaft 150 extends distally through an opening (aligned with the drive axis DA) in the distal end wall 130 and is secured to the bearing 146. The bearing 146 supports the drive shaft 150 and allows the drive shaft to rotate in the housing 122. The diameter of the opening in the distal end wall 134 is larger than the outer diameter of the distal end portion of the drive shaft 150 in order to provide the necessary clearance to allow the drive shaft to rotate therein.

Figure 4:
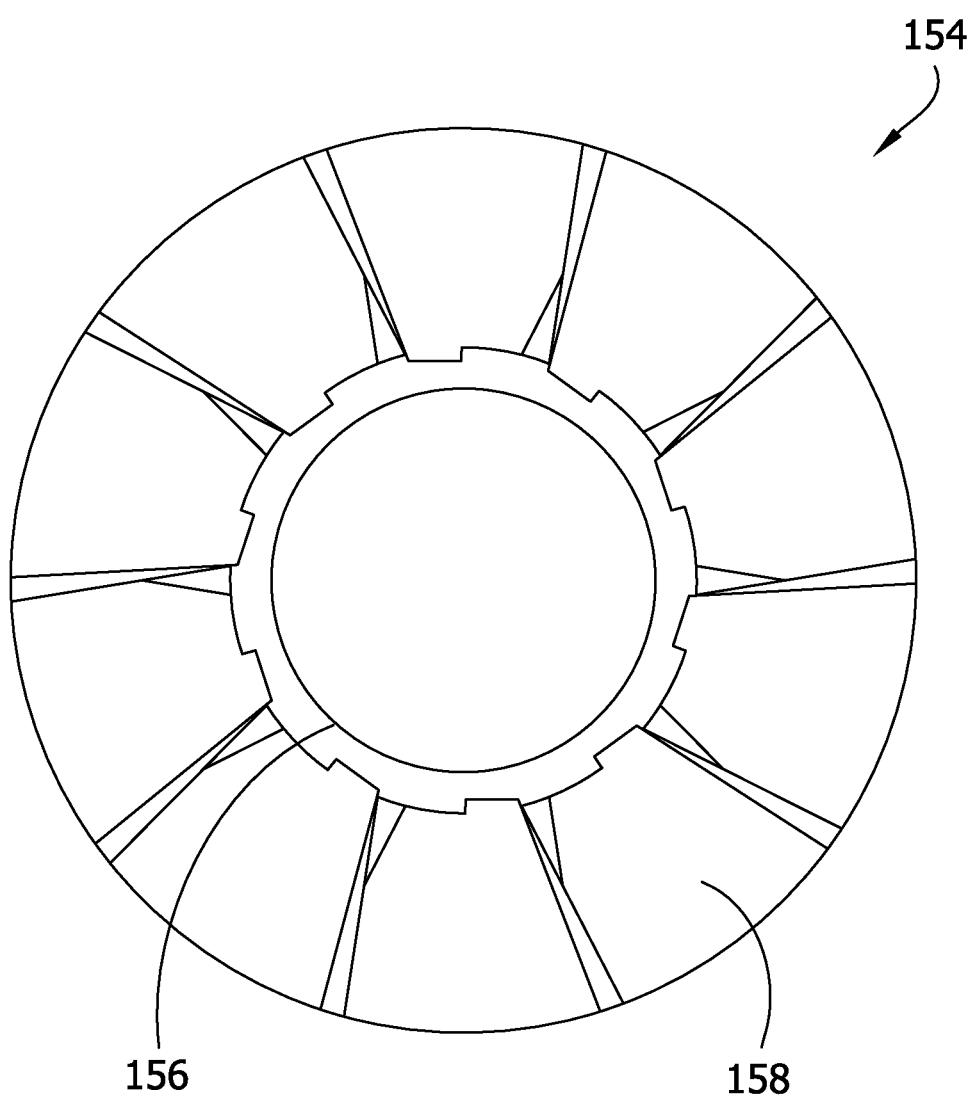
FIG. 4 is a front elevational view of an impeller of the turbine of FIG. 2.

The rotor 124 includes at least one impeller 154 secured to the drive shaft 140 and extending radially outward (e.g., away from the drive axis DA) therefrom into the inner passageway 166. The inner diameter of the intermediate wall 160 is larger than the outer diameter of the impeller 154 in order to provide the necessary clearance to allow the impeller, and thereby the drive shaft 150, to rotate within the inner passageway. In the illustrated embodiment, the rotor 124 includes two impellers 154 longitudinally spaced apart along the drive shaft 150, although the rotor can have more or less impellers. The impellers 154 are connected to the intermediate portion of the drive shaft 150. As shown in FIG. 4, each impeller 154 has a annular ring 156 that connects the impeller to the drive shaft 150 and a plurality of blades 158 extending radially outward from the ring. Each blade 158 is at an angle relative to a rotational plane the impeller 154 rotates in (e.g., a plane normal to the drive axis DA). In the illustrated embodiment, the impeller 154 has ten blades 158 circumferentially spaced on the annular ring 156. It is understood the impeller 154 may have more or less blades 158.

The rotor 124 is operatively connected (e.g., attached) to the drive shaft 26 of the distal body portion 12a to drive rotation of the tissue removing element 24. As explained in more detail below, the drive shaft 26 of the distal body portion 12a is configured to rotate and is connected to the tissue removing element 24 such that rotation of the drive shaft rotates the tissue removing element. In one embodiment, a proximal end portion of the drive shaft 26 extends along and is fixed to the driver shaft 150 by any suitable means, such as, but not limited to, an adhesive. In other embodiments, the drive shaft 26 may be mechanically fastened to the drive shaft 150. In one embodiment, the distal end portion of the drive shaft 150 includes a receptacle (not shown) that receives the proximal end portion of the drive shaft 26. The proximal end portion of the drive shaft 26 is fixed within the receptacle to attach the drive shaft to the drive shaft 150.

In one embodiment, the turbine 118 includes flexible proximal and distal end portions (not shown) which extend proximally and distally, respectively from the proximal and distal ends of the housing 122 to provide a strain relief function for the turbine 118 by alleviating tension applied to the turbine as the catheter 10 is bent (e.g., maneuvered) during use. The housing 122 may be formed from polyether ether ketone (PEEK). The impeller 154 may be formed from a metal sheet and bent into shape. For example, the impeller 154 may be laser cut from a stainless steel sheet and bent into shape.

Figure 5:
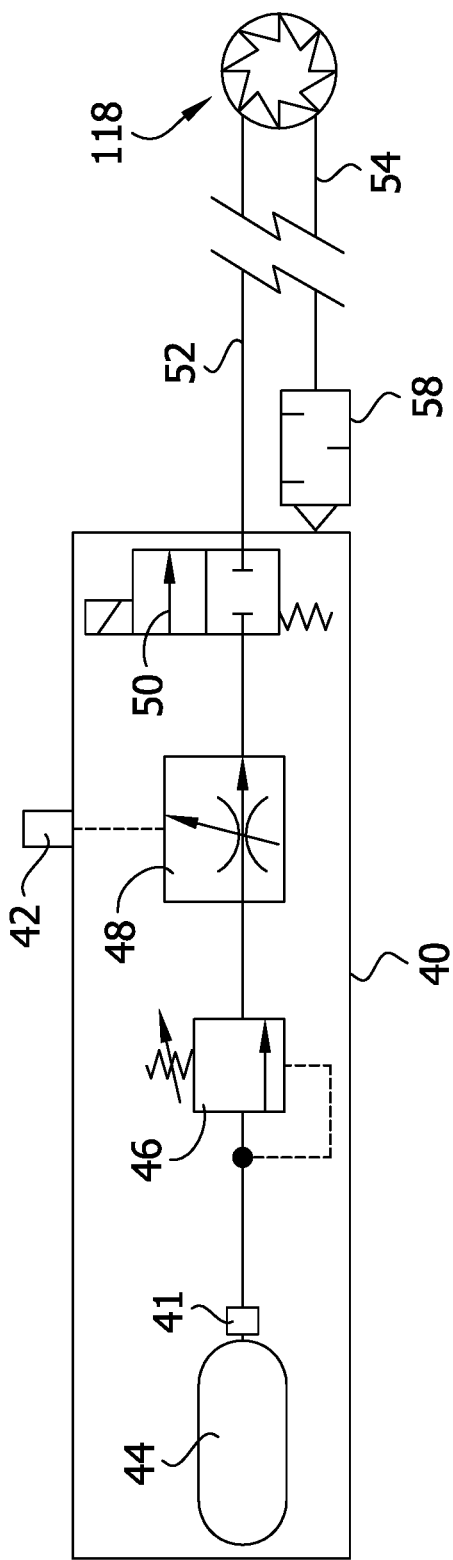
FIG. 5 is a block diagram of one embodiment of a catheter that does not impart a vacuum on the turbine.
Figure 6:
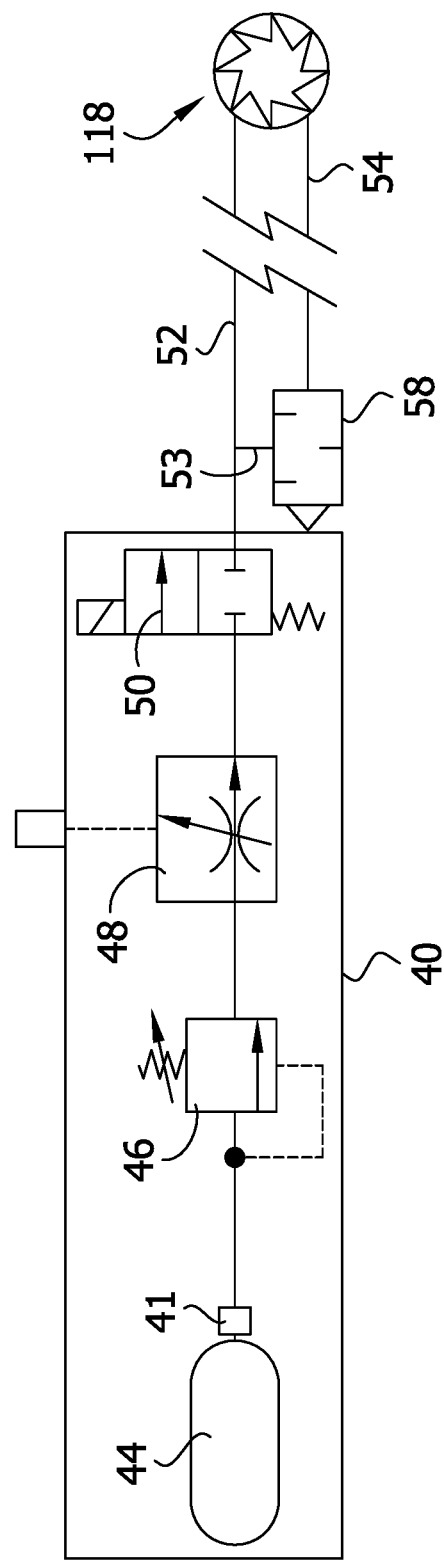
FIG. 6 is a block diagram of another embodiment of a catheter that imparts a vacuum on the turbine.

Referring to FIGS. 1, 5 and 6, the catheter 10 further comprises a handle 40 secured at a proximal end portion 14 of the catheter. The handle 40 supports an actuator 42 (e.g., a knob, a lever, a button, a dial, a switch, or other device)

configured for selectively actuating the turbine 118 to selectively drive rotation of the tissue removing element 24 from a location outside the body lumen (e.g., remote from the turbine). In one embodiment, the turbine 118 is disposed about 100 cm (about 39.4 inches) from the handle 40, although other distances are within the scope of the present disclosure. The illustrated handle 40 includes a connection fitting 41 configured to releasable connect the handle to a source of pressurized propellant, a pressure regulator 46 configured to normalize the pressure of the propellant from the source of pressurized propellant, a needle valve 48 configured to control the flow of the pressurized propellant, and a two way valve 50 all fluidly connected to one another in series. In the illustrated embodiment, the source of pressurized propellant is a canister 44 releasably connected to the connection fitting 41 of the handle 40 and supported by the handle (broadly, the handle includes the pressurized canister). In this embodiment, the connection fitting 41 may be a quick change fitting to allow canisters 44 to be quickly and easily attached and detached from the handle 40. The canister 44 holds the propellant under pressure. In another embodiment, the source of pressurized propellant may come from a source external of the handle 40 that has a line (not shown) connected to the connection fitting 41. Preferably, the propellant is carbon dioxide ($CO_2$), although any suitable pressurized propellant (e.g., pressurized gas) may be used with the catheter 10 to power the turbine 118.

In the illustrated embodiment, the actuator 42 is operatively connected to the needle valve 48 to selectively control the flow the pressurized propellant. The actuator 42 is disposed on the handle 40 for movement relative to the handle to selectively fluidly couple the source of pressurized propellant (e.g., canister 44) to the turbine 118. The actuator 42 selectively operates the needle valve 48 to selectively control the flow of the propellant to the turbine 118. Preferably, the actuator 42 is movable with respect to the handle 40 to a non-actuating position and a plurality of actuated positions for variably adjusting the flow of the pressurized propellant through the needle valve 48 and, thus, the speed of the turbine 118. In the non-actuated position, the actuator 42 operates the needle valve 48 such that the needle valve is closed and no propellant can pass there-through. This prevents the turbine 118 and, thereby, the tissue removing element, from rotating. In each of the actuated positions, the actuator 42 controls the degree to which the needle valve 48 is open to adjust the amount of flow through the needle valve and, thus, the speed at which the turbine 118 rotates the tissue removing element 24. It is understood that other suitable actuators, including but not limited to touchscreen actuators, wireless control actuators, automated actuators directed by a controller, etc., may be suitable to selectively actuate the motor in other embodiments. Moreover, preferably, the pressure setting of the pressure regulator 46 is also adjustable, such as by a second actuator (not shown), so that the pressure of the propellant supplied to the turbine 118 can vary. By adjust the pressure and flow of the pressurized propellant, with the pressure regulator 46 and needle valve 48, respectively, the torque and speed of the turbine 118 can be adjusted to suit the desired rotational speed and torque of the tissue removing element 24.

Figure 3A:
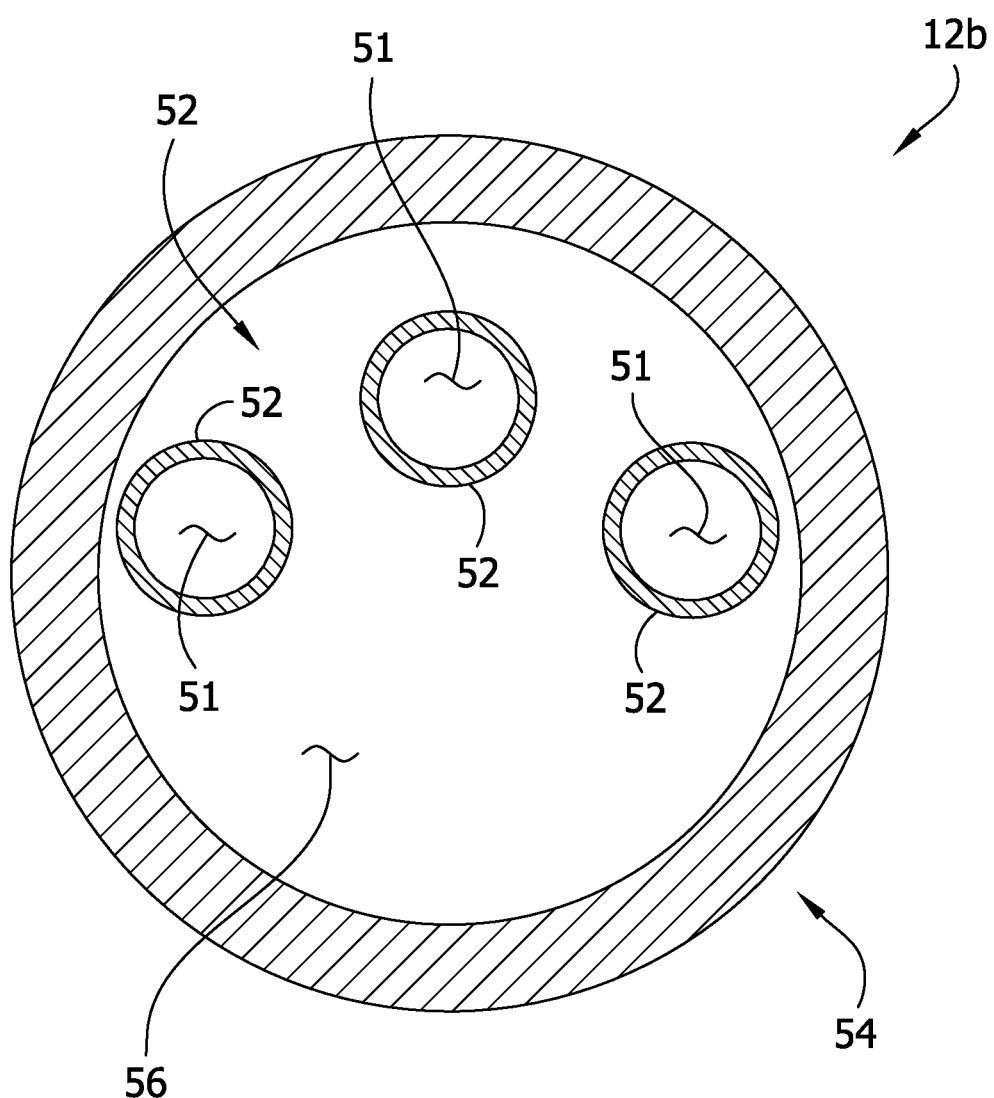
FIG. 3A is a cross section taken through line 3A-3A in FIG. 3.

Referring to FIGS. 1, 3 and 3A, the proximal body portion 12b extends distally from the handle 40 to the turbine 118 and fluidly connects the handle to the turbine. The proximal body portion 12b includes a supply line 52 defining a supply fluid passageway 51 (FIG. 3A) that provides fluid communication between the handle 40, specifically the two way valve 50, to deliver the flow of pressurized propellant from the source of pressurized propellant (e.g., canister 44) to the turbine 118. As shown in FIGS. 2 and 3, a distal end portion of the supply line 52 extends through a proximal opening defined by the tip 138 of the conical wall 136. The distal end portion of the supply line 52 extends distally through tip 138 and the outlet chamber 142 to the divider wall 134. In particular, the distal end of the supply line 52 is attached to the divider wall 134 at the inlet opening 168 such that the supply fluid passageway 51 is fluidly connected to the outer passageway 162. In the illustrated embodiment, there are three inlet openings 168 circumferentially and evenly spaced apart on the divider wall 134 and the distal end portion of the supply line 52 branches off into three distal supply lines 52a, each distal supply line connected to one of the inlet openings. This provides a more uniform initial distribution of propellant in the rotor chamber 140. In other embodiments, there may be more or less than three inlet openings 168 and distal supply lines 52a.

Figure 7:
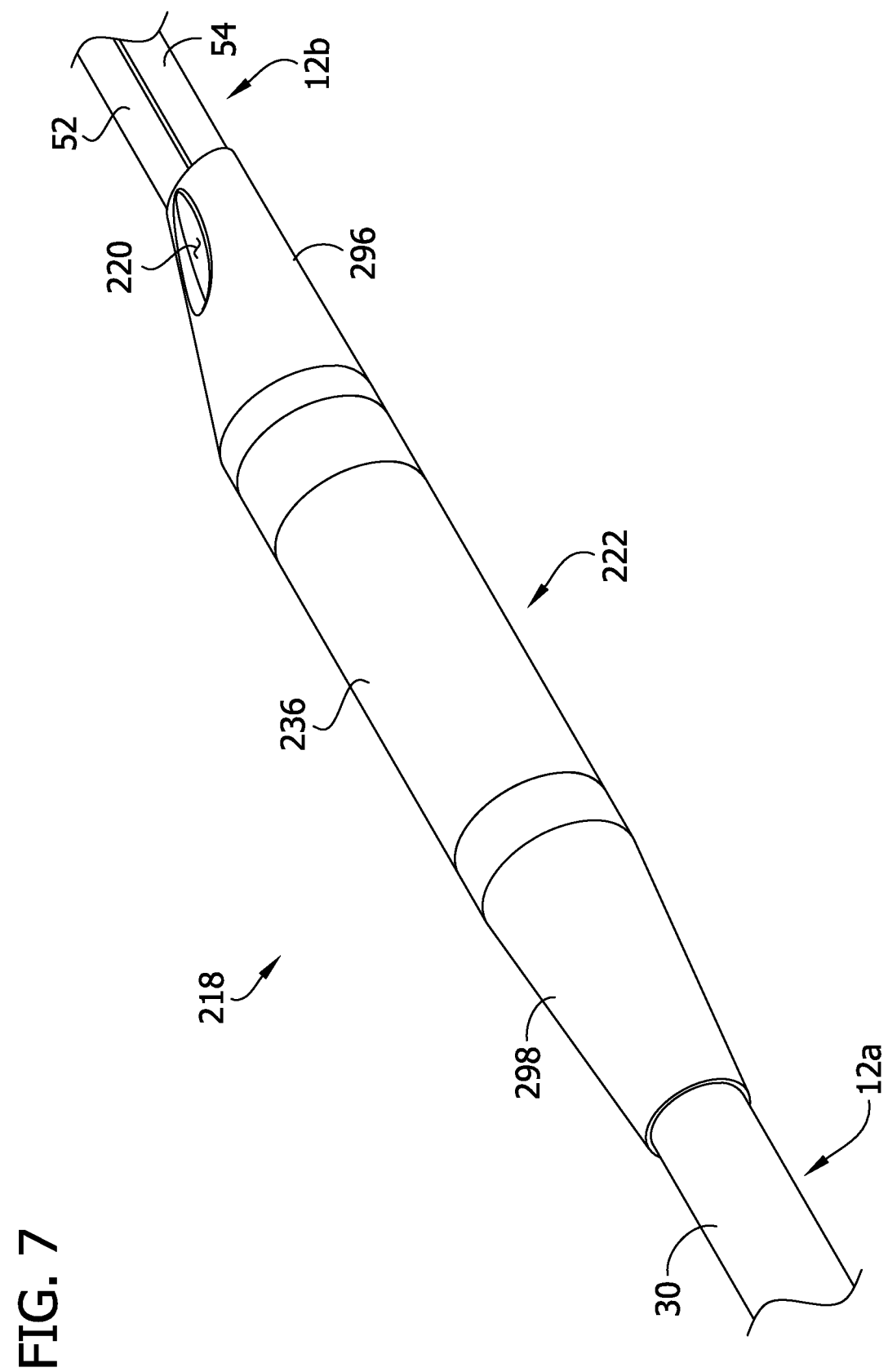
FIG. 7 is a perspective of another embodiment of a turbine of the present disclosure.
Figure 8:
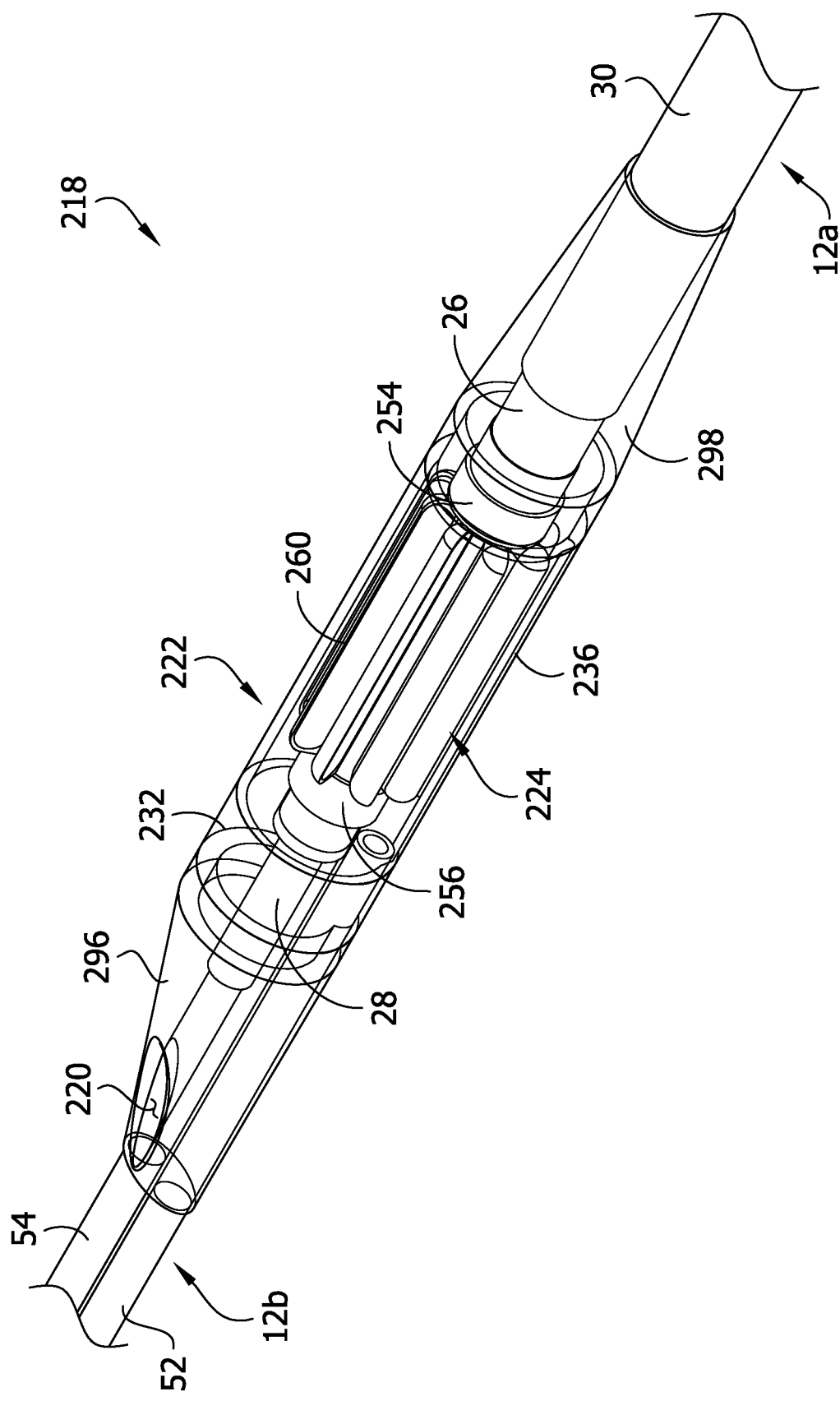
FIG. 8 is a perspective of the turbine of FIG. 7, with portions thereof being transparent to show internal components.

The proximal body portion 12b also includes a return line 54 extending along at least a portion of the proximal body portion and defining a return fluid passageway 56 (FIG. 3A) that provides fluid communication between the turbine 118 and an exhaust 58 (FIG. 1) of the catheter 10 to convey the pressurized propellant from the turbine to the exhaust. As shown in FIG. 3, the distal end of the return supply line 54 extends proximally from the proximal opening defined by the tip 138 of the conical wall 136. In particular, the distal end of the return supply line is attached to the conical wall 136 at the tip 138 such that the return fluid passageway 56 is fluidly connected to the outlet chamber 142. In the illustrated embodiment, the supply line 52 extends through the return line 54 such that the supply line is disposed in the return fluid passageway 56 (e.g., the return line encases the supply line). In this manner, the proximal body portion 12b is a multi-lumen line that transports the pressurized propellant to and from the turbine 118. In other embodiments, the supply line 52 and return line 54 may be in a side-by-side arrangement (FIG. 7).

Referring to FIGS. 1, 5 and 6, the exhaust 58 is configured to release the pressurized propellant into the surrounding atmosphere after the propellant has powered (e.g., flowed through) the turbine 118. The exhaust 58 may be part of the handle 40 or the exhaust may be a separate component that is spaced apart from the handle. As shown in FIG. 5, in one embodiment, the exhaust 58 is connected in series with the source of pressurized propellant (e.g., canister 44) and the turbine 118 such that, in operation, the propellant flow from the source of pressurized propellant, through the turbine and out through the exhaust. As shown in FIGS. 1 and 6, in one embodiment, the exhaust 58 is connect in parallel with the turbine 118 so that the exhaust imparts a vacuum in the return fluid passageway 54 to increase the pressure drop across the turbine, thereby increasing the rotational speed and/or torque of the rotor. In this embodiment, the proximal body portion 12b of the catheter 10 includes an exhaust supply line 53 fluidly connected to the source of pressurized propellant and the exhaust 58 such that a portion of the pressurized propellant supplied by the source (e.g., canister 44) is diverted away from the turbine 118 and flows directly into and then out of the exhaust. This embodiment still includes the return line 54 to transport the propellant from the turbine 118 to the exhaust 58. The exhaust 58 expels both the diverted propellant from the exhaust supply line 53 and the propellant from the return line 54 at the same time. As a result of the exhaust 58 directly expelling a portion of the propellant from the source of pressurized propellant (e.g., canister 44) and also being connected to the return line 54, a vacuum forms in the return line 54 which draws the propellant from the turbine 118. Specifically, the exhaust 58 constricts the flow of pressurized propellant from the exhaust supply line 53 to create a Venturi Effect before the propellant from the return line 54 mixes with the propellant from the exhaust supply line (see FIG. 1). As a result, the pressure in the return line 54 is reduced (from normal atmospheric pressure) which increases the pressure drop across the turbine 118—increasing the efficiency of the turbine.

Referring to FIGS. 14-21, as mentioned above, the distal body portion 12a of the catheter 10 includes the elongate inner liner 28, the elongate drive shaft 26 and the sheath 30. The sheath 30 comprises a tubular sleeve configured to isolate and protect a subject's arterial tissue within a body lumen from at least a portion of the rotating drive shaft 26 and inner liner 28. The inner diameter of the sheath 30 is sized to provide clearance for the drive shaft 26. The space between the sheath 30 and the drive shaft 26 allows for the drive shaft to rotate within the sheath and provides an area for saline perfusion between the sheath and drive shaft. The outer diameter of the sheath 30 may be sized to provide clearance with an inner diameter of a guide catheter (not shown) for delivering the catheter 10 to the desired location in the body lumen. In one embodiment, the sheath has an inner diameter of about 0.050 inches (1.27 mm) and an outer diameter of about 0.055 inches (1.4 mm). The sheath can have other dimensions without departing from the scope of the disclosure. In one embodiment, the outer sheath is made from polytetrafluorethylene (PTFE). Alternatively, the sheath may comprise a multi-layer construction. For example, the outer sheath may comprise an inner layer of perfluoroalkox (PFA), a middle braided wire layer, and an outer layer of Pebax.

The drive shaft 26 may comprise a tubular stainless steel coil configured to transfer rotation and torque from the turbine 118 to the tissue-removing element 24. Configuring the drive shaft 26 as a coiled structure provides the drive shaft with a flexibility that facilitates delivery of the catheter 10 through the body lumen. Also, the coil configuration allows for the rotation and torque of the drive shaft 26 to be applied to the tissue-removing element 24 when the catheter 10 is traversed across a curved path. The stiffness of the drive shaft 26 also impacts the ease at which the coil is traversed through the body lumen as well as the coil's ability to effectively transfer torque to the tissue-removing element 24. In one embodiment, the drive shaft 26 is relatively stiff such that axial compression and extension of the coil is minimized during movement of the catheter 10 through a body lumen. In one embodiment, the drive shaft 26 has an inner diameter of about 0.023 inches (0.6 mm) and an outer diameter of about 0.035 inches (0.9 mm). The drive shaft 26 may have a single layer construction. For example, the drive shaft may comprise a 7 filar (e.g., wire) coil with a lay angle of about 30 degrees. Alternatively, the drive shaft 26 could be configured from multiple layers without departing from the scope of the disclosure. For example, the drive shaft 26 may comprise a base coil layer and a jacket (e.g., Tecothane™) disposed over the base layer. In one embodiment, the drive shaft comprises a 15 filar coil with a lay angle of about 45 degrees. The Tecothane™ jacket may be disposed over the coil. Alternatively, the drive shaft 26 may comprise a dual coil layer configuration which also includes an additional jacket layer over the two coil layers. For example, the drive shaft may comprise an inner coil layer comprising a 15 filar coil with a lay angle of about 45 degrees, and an outer coil layer comprising a 19 filar coil with a lay angle of about 10 degrees. Drive shaft 26 having other configurations are also envisioned.

Figure 17:
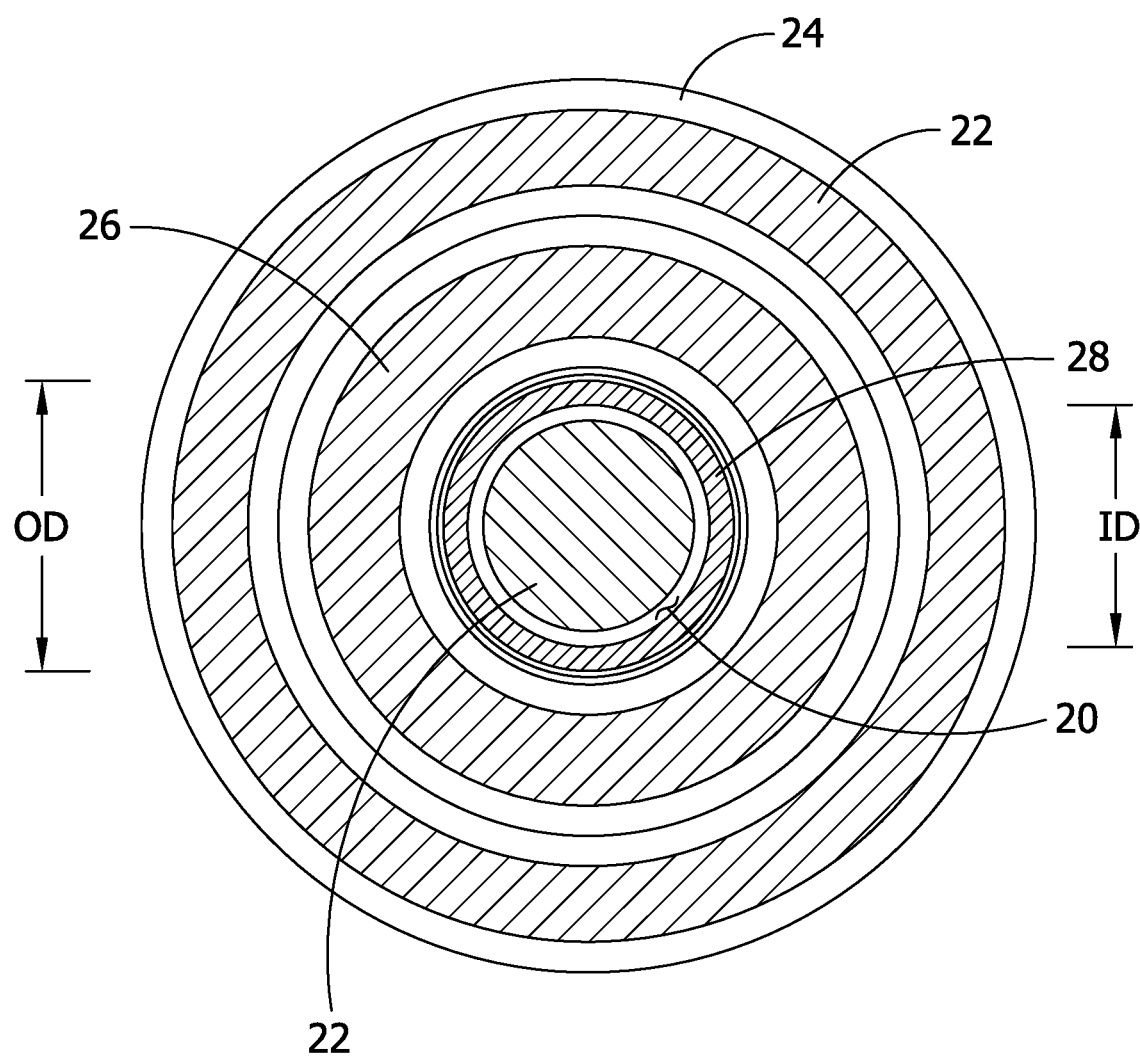
FIG. 17 is a cross section taken through line 17-17 in FIG. 15.

The inner liner 28 comprises a multiple layer tubular body configured to isolate the guidewire 22 from the drive shaft 26, the tissue-removing element 24, and, in some embodiments, the drive shaft 150. The inner liner 28 is fixedly attached to the turbine 118 to prevent relative movement between the inner liner and turbine. Thus, the inner liner 28 remains stationary and is prevented from translating relative to the turbine 118. Additionally, rotation of the inner liner 28 by the rotation of the drive shaft 26 is prevented. The inner liner 28 has an inner diameter ID that is sized to pass the guidewire 22 (FIG. 17). The inner liner 28 protects the guidewire 22 from being damaged by the rotation of the drive shaft 150 and drive shaft 26 by isolating the guidewire from the rotatable drive shaft and drive shaft. The inner liner 28 also extends past the tissue-removing element 24 to protect the guidewire 22 from the rotating tissue-removing element. Thus, the inner liner 28 is configured to prevent any contact between the guidewire 22 and the components of the catheter 10 that rotate around the guidewire. Therefore, any metal-to-metal engagement is eliminated by the inner liner 28. This isolation of the drive shaft 150, drive shaft 26, and tissue-removing element 24 from the guidewire 22 also ensures that the rotation of the drive shaft 26 and tissue-removing element 24 is not transferred or transmitted to the guidewire 22. As a result, a standard guidewire 22 can be used with the catheter 10 because the guidewire does not have to be configured to withstand the torsional effects of the rotating components. Additionally, by extending through the tissue-removing element 24 and past the distal end of the tissue-removing element, the inner liner 28 stabilizes the tissue-removing element by providing a centering axis for rotation of the tissue-removing element about the inner liner.

Figure 18:
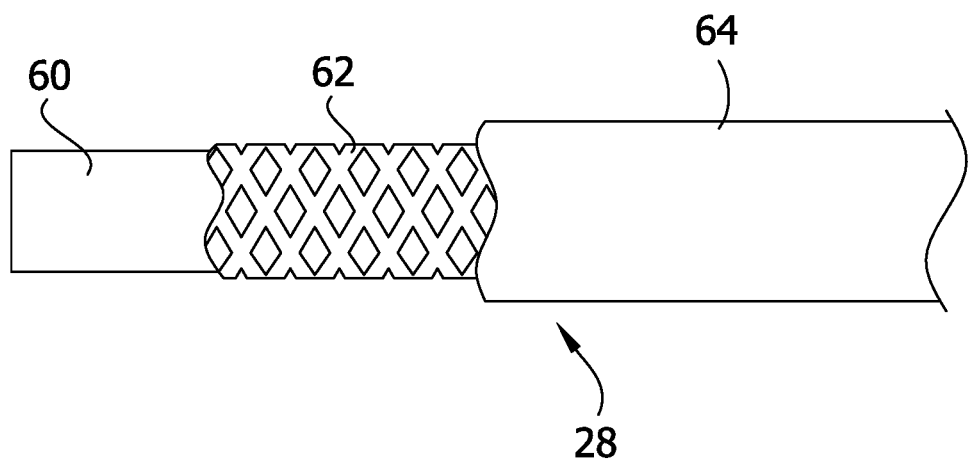
FIG. 18 is a fragmentary elevation of an inner liner of the catheter of FIG. 14 with portions broken away to show internal details.
Figure 19:
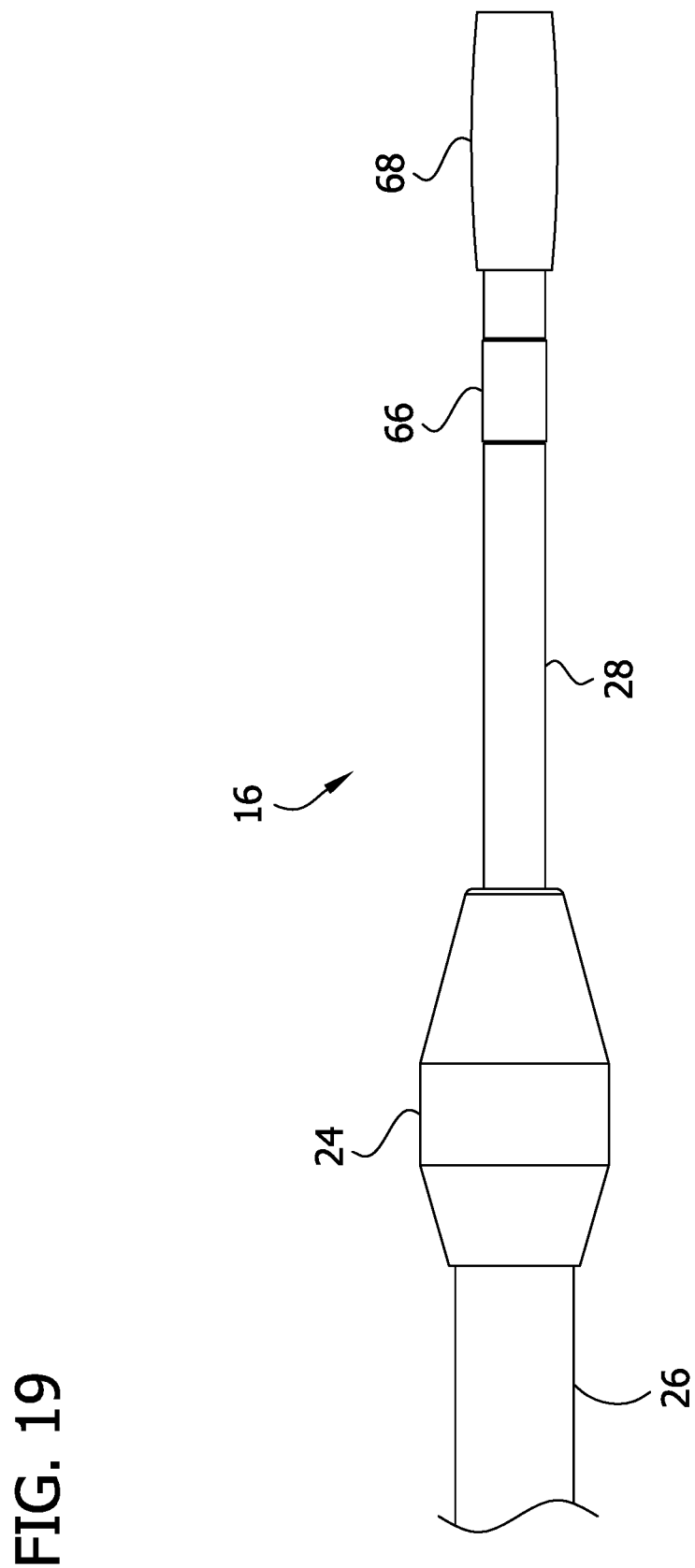
FIG. 19 is an enlarged elevation of a distal end portion of the catheter of FIG. 14 showing an atraumatic tip on the inner liner.
Figure 20:
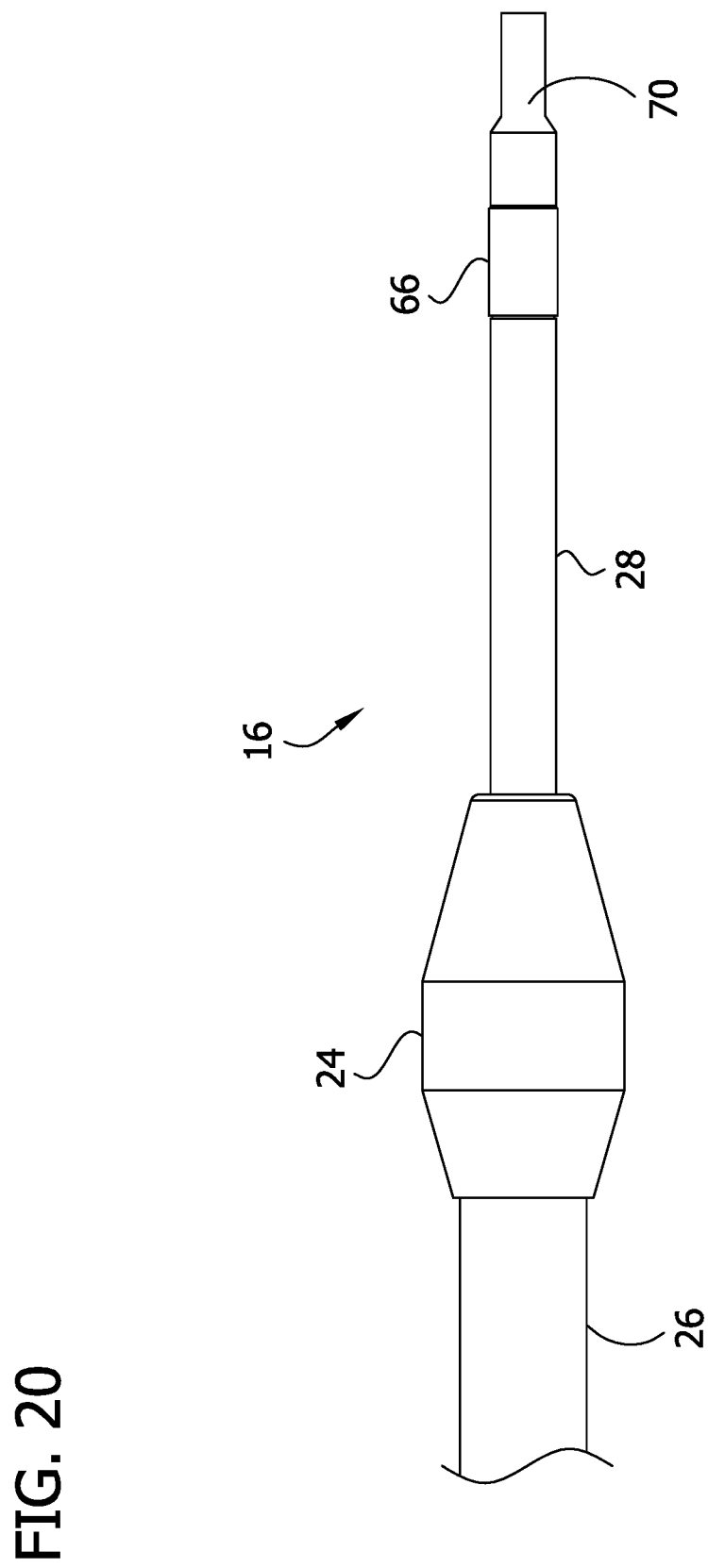
FIG. 20 is an enlarged elevation of a distal end portion of the catheter of FIG. 14 showing a tapered tip on the inner liner.

Referring to FIG. 18, in one embodiment, the inner liner 28 comprises an inner PTFE layer 60, an intermediate braided layer 62 comprised of stainless steel, and an drive shaft 64 of polyimide. The PTFE inner layer 60 provides the inner liner 28 with a lubricous interior which aids in the passing of the guidewire 22 though the inner liner. The braided stainless steel intermediate layer 62 provides rigidity and strength to the inner liner 28 so that the liner can withstand the torsional forces exerted on the inner liner by the drive shaft 26. In one embodiment, the intermediate layer 62 is formed from 304 stainless steel. The outer polyimide layer 64 provides wear resistance as well as having a lubricous quality which reduces friction between the inner liner 28 and the drive shaft 26. Additionally, a lubricious film, such as silicone, can be added to the inner liner 28 to reduce friction between the inner liner and the drive shaft 26. In one embodiment, the inner liner 28 has an inner diameter ID of about 0.016 inches (0.4 mm), an outer diameter OD of about 0.019 inches (0.5 mm), and a length of about 39.4 inches (about 100 cm). The inner diameter of the inner liner 28 provides clearance for the standard 0.014 inch guidewire 22. The outer diameter of the inner liner 28 provides clearance for the drive shaft 150, drive shaft 26, and tissue-removing element 24. Having a space between the inner liner 28 and the drive shaft 26 reduces friction between the two components as well as allows for saline perfusion between the components.

In one embodiment, a marker band 66 (FIG. 15) is provided on an exterior surface of the distal end of the inner liner 28. The marker band 66 configures the tip of the inner liner 28 to be fluoroscopically visible which allow a physician to verify the position of the liner during a medical procedure. In this embodiment, the distal end of the inner liner 28 may be laser cut to provide a low profile tip. In one embodiment, the marker band 66 comprises a strip of platinum iridium.

It is further envisioned that the distal end of the inner liner 28 can have other constructions without departing from the scope of the present disclosure. For example, an atraumatic tip 68 (FIG. 19) may be attached to the distal end of the inner liner 28. The atraumatic tip 68 provides a soft, low profile distal end to facilitate delivery of the inner liner 28 through the body lumen without causing trauma. The atraumatic tip 68 may have a maximum outer diameter of about 0.02 inches (0.6 mm). Other sizes of the atraumatic tip 68 are also envisioned. In another embodiment, a tapered tip 70 (FIG. 20) may be attached to the distal end of the inner liner 28. The tapered tip 70 may be formed from a layer of material configured to protect the distal end of the inner liner 28.

Figure 15:
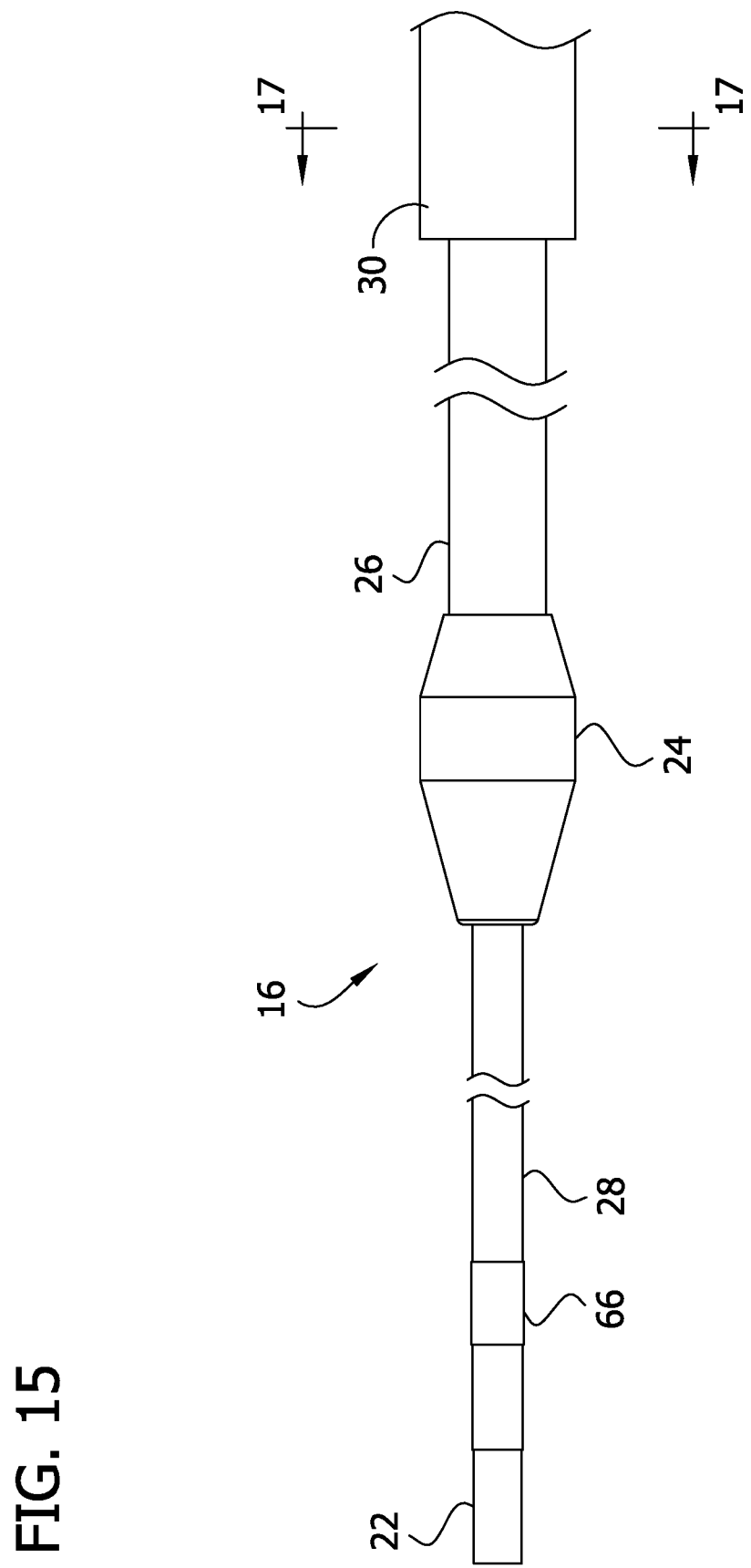
FIG. 15 is an enlarged elevation of a distal end portion of the catheter of FIG. 14.

Referring to FIG. 15, the tissue-removing element 24 extends along the longitudinal axis LA of the catheter 10 from a proximal end adjacent the distal end portion of the drive shaft 26 to an opposite distal end. The tissue-removing element 24 is operatively connected to the turbine 118, via the drive shaft 26, for being rotated by the turbine. When the catheter 10 is inserted into the body lumen and the turbine 118 is activated to rotate the drive shaft 26 thereby rotating the tissue-removing element 24. Any suitable tissue-removing element 24 for removing tissue in the body lumen as it is rotated may be used. In one embodiment, the tissue-removing element 24 comprises an abrasive burr configured to abrade tissue in the body lumen when the turbine 118 rotates the abrasive burr. The abrasive burr 24 may have an abrasive outer surface formed, for example, by a diamond grit coating, surface etching, or the like. In one embodiment, the tissue-removing element 24 comprises a stainless steel spheroid body with an exterior surface including 5 μm of exposed diamond crystals. The tissue-removing element 24 may also be radiopaque to allow the tissue-removing element to be visible under fluoroscopy. In other embodiments, the tissue-removing element can comprise one or more cutting elements having smooth or serrated cutting edges (e.g., an annular cutting edge), a macerator, a thrombectomy wire, etc.

Figure 16:
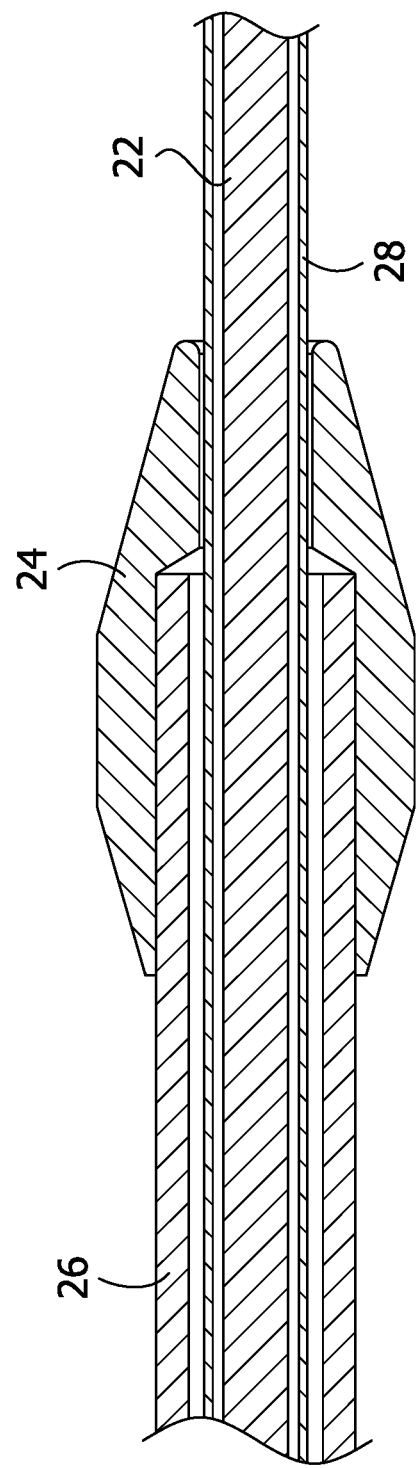
FIG. 16 is an enlarged fragmentary longitudinal cross section of the distal end portion of the catheter of FIG. 15.
Figure 21:
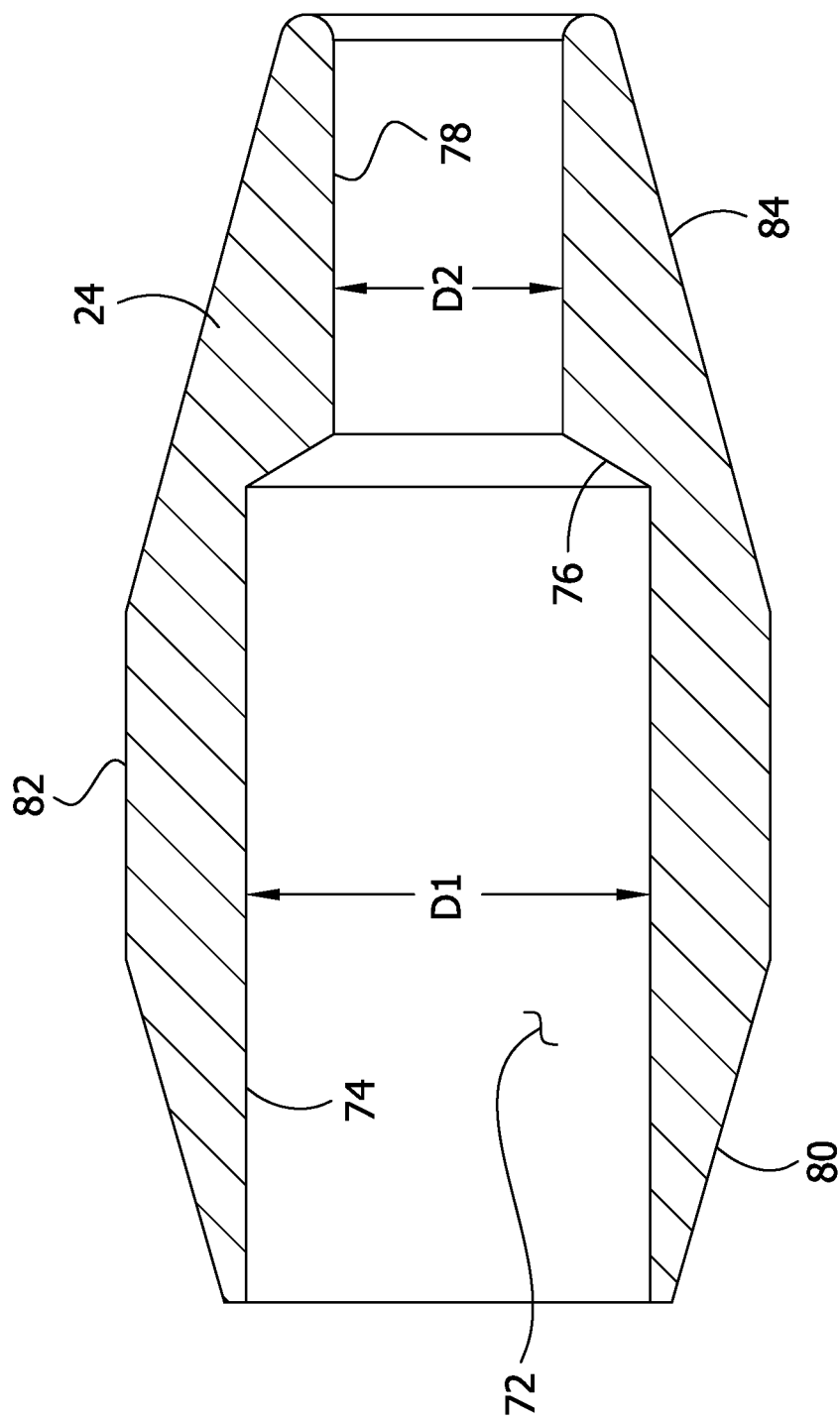
FIG. 21 is an enlarged longitudinal cross section of a tissue removing element of the catheter of FIG. 14.

Referring to FIG. 21, in one embodiment, a cavity 72 extends longitudinally through the tissue-removing element 24 such that the tissue-removing element defines openings at its proximal and distal ends. The cavity 72 receives a portion of the drive shaft 26 for mounting the tissue-removing element 24 to the drive shaft (FIG. 16). The cavity 72 includes a first diameter portion 74 extending from the proximal end of the tissue-removing element 24, a tapered diameter portion 76 extending from the first diameter portion toward the distal end of the tissue-removing element, and a second diameter portion 78 extending from the tapered diameter portion to the distal end of the tissue-removing element. The diameters of the first and second diameter portions 74, 78 are constant along their lengths. In the illustrated embodiment, a diameter D1 of the first diameter portion 74 is larger than a diameter D2 of the second diameter portion 78. In one embodiment, the diameter D1 of the first diameter portion 74 is about 0.035 inches (0.9 mm), and the diameter D2 of the second diameter portion 78 is about 0.022 inches (0.56 mm). The tapered diameter portion 76 provides a transition between the first and second diameter portions 74, 78. The drive shaft 26 is received in the first diameter portion 74 and a distal end of the drive shaft abuts the tapered diameter portion 76 (FIG. 16). The tissue-removing element 24 can be fixedly attached to the distal end of the drive shaft 26 by any suitable means. In one embodiment an adhesive bonds the tissue-removing element 24 to the drive shaft 26. The inner liner 28 extends through the drive shaft 26 and the second diameter portion 78 of the tissue-removing element 24. The second diameter portion 78 is sized to pass the inner liner 28 with a small clearance. The inner diameter D2 provides clearance between the tissue-removing element 24 and inner liner 28 to reduce friction between the components and allow a space for saline perfusion. Accordingly, the tissue-removing element 24 is shaped and arranged to extend around at least a portion of the drive shaft 26 and inner liner 28 and thus provides a relatively compact assembly for abrading tissue at the distal end portion of the catheter 10.

The exterior surface of the tissue-removing element 24 includes a proximal segment 80, a middle segment 82, and a distal segment 84. A diameter of the proximal segment 80 increases from the proximal end of the tissue-removing element 24 to the middle segment 82. The middle segment has a constant diameter and extends from the proximal segment 80 to the distal segment 84. The diameter of the distal segment 84 tapers from the middle segment 82 to the distal end of the tissue-removing element 24. The tapered distal segment 84 provides the tissue-removing element 24 with a general wedge shape configuration for wedging apart constricted tissue passages as it simultaneously opens the passage by removing tissue using the abrasive action of the tissue-removing element. The distal end of the tissue-removing element 24 is also rounded to provide the tissue-removing element with a blunt distal end.

Referring to FIGS. 1 and 14, to remove tissue in the body lumen of a subject, a practitioner inserts the guidewire 22 into the body lumen of the subject, to a location distal of the tissue that is to be removed. Subsequently, the practitioner inserts the proximal end portion of the guidewire 22 through the distal end of the guidewire lumen 20 of the inner liner 28 and through the turbine 118 so that the guidewire extends through the guidewire port 120 in the turbine to exit the catheter 10. With the catheter 10 loaded onto the guidewire 22, the practitioner advances the catheter along the guidewire until the tissue-removing element 24 is positioned proximal and adjacent the tissue. When the tissue-removing element 24 is positioned proximal and adjacent the tissue, the practitioner actuates the turbine 118 using the actuator 42 to open the needle valve 48 to allow pressurized propellant from the source of pressurized propellant (e.g., canister 44), which was previously fluidly connected to the handle 40, to flow through the turbine 118 and rotate the rotor 124, the drive shaft 26, and the tissue-removing element mounted on the drive shaft. The tissue-removing element 24 abrades (or otherwise removes) the tissue in the body lumen as it rotates. While the tissue-removing element 24 is rotating, the practitioner may selectively move the catheter 10 distally along the guidewire 22 to abrade the tissue and, for example, increase the size of the passage through the body lumen. The practitioner may also move the catheter 10 proximally along the guidewire 22, and may repetitively move the components in distal and proximal directions to obtain a back-and-forth motion of the tissue-removing element 24 across the tissue. When the practitioner is finished using the catheter 10, the catheter can be removed from the body lumen. In one embodiment, the a 12 gram canister 44 of $CO_2$ is the source of pressurized propellant fluidly connected to the catheter 10 which can power the turbine 118 continuously at about 80,000 RPM with a torque of about 1.5 mNm for about 8.5 to 20 minutes. $CO_2$ is one of the preferred propellants because it can be easily absorbed by the blood of a subject should any $CO_2$ leak or escape from the catheter 10 (e.g., turbine 118, proximal body portion 12b, etc.) and into the body lumen during use.

When the practitioner operates the actuator 42 to open and set the position of the needle valve 48, the pressurized propellant flows from the source of pressurized propellant through the supply line 52 and into the rotor chamber 140 of the turbine 118. Specifically, the propellant flows through the outer passageway 162, through the transition section 164, through the inner passageway and into the outlet chamber 162. The propellant flows distally through the outer passageway 162, is turned around (e.g., 180° change in direction) as the propellant flows through the transition section 164, and then flows proximally through the inner passageway 166. As the propellant moves through the inner passageway 166, the propellant contacts the impellers 154 which rotates the rotor 124. The rotor 124 can be configured to rotate clockwise or counter-clockwise. After the propellant rotates the rotor 124 in the inner passageway 160, the propellant moves through the outlet chamber 162 and into the return line 54 toward the exhaust 58, where the propellant is vented into the surrounding atmosphere. If the exhaust 58 is configured to impart a vacuum on the return line 54, when the actuator 42 is operated to start the flow of propellant in the supply line 52, a portion of the propellant will flow directly to the exhaust via the exhaust supply line 53 to create the vacuum, as described above.

The guidewire port 120 allows the catheter 10 to be used in a rapid exchange and single operator exchange procedures. Since the turbine 118 is distally spaced from the handle 40 and defines the guidewire port 120 (e.g., proximal end of the guidewire lumen), the guidewire lumen is considerably shorter than the overall length of the catheter 10. This enables the catheter 10 to be removed from the body lumen in a rapid exchange or single operator exchange procedure without pulling the guidewire 22 out of the body lumen together with the catheter because the length of the guidewire is longer than the length of the guidewire lumen 20 of the catheter. Thus, at least a portion of the guidewire 22 is exposed at all times and may be grasped by the practitioner. Moreover, because the turbine 118 is distally spaced from the handle 40, the overall length of the rotational drive shaft (e.g., drive shaft 26) that extends along the elongate body 12 is reduced.

Referring to FIGS. 7-13, another embodiment of a turbine for use with the catheter 10 is generally indicated at 218. It is understood that turbine 218 is interchangeable with turbine 118 such that either turbine can be used with the embodiments of the catheter 10 described herein. Accordingly, the references to turbine 118 as part of catheter 10 discussed above apply equally to turbine 218. The turbine 218 of the second embodiment includes a housing (e.g., stator) 222 enclosing a rotor 224 configured to rotate within the housing, the rotor being operatively connected to the tissue removing element 24 such that rotation of the rotor in the housing drives rotation of the tissue removing element. In one embodiment, the turbine 218 is configured to rotate the tissue removing element 24 at speeds of greater than about 80,000 RPM while generating a torque of about 1.5 mNm. In one embodiment, the turbine 218 is a microturbine that is sized and arranged for being received in the body lumen of the subject. In one embodiment, the turbine 218 has an outer diameter from about 0.5 mm to about 4 mm. The turbine 218 is sized such that it can be received within a guide catheter (not shown). In one embodiment, the turbine 218 is sized so that the catheter 10 can be received in a 7 F (about 2 mm) or smaller diameter guide catheter. In another embodiment, the turbine 218 is sized so that the catheter 10 can be received in a 6 F (about 1.8 mm) or smaller diameter guide catheter. The turbine 218 is cannulated such that the turbine is a through-hole turbine. In this manner, the turbine 218 defines a portion of the guidewire lumen 20 that extends along a drive axis DA (FIG. 13) of the turbine. The portion of the guidewire lumen 20 defined by the turbine 218 is aligned with the portion of the guidewire lumen defined by the inner liner 28 of the distal body portion 12a (e.g., the drive axis DA is coaxial with the longitudinal axis LA of the catheter 10) so that the guidewire 22 may extend from the distal body portion into the turbine or vice versa without bending, curving, or changing direction.

Figure 11:
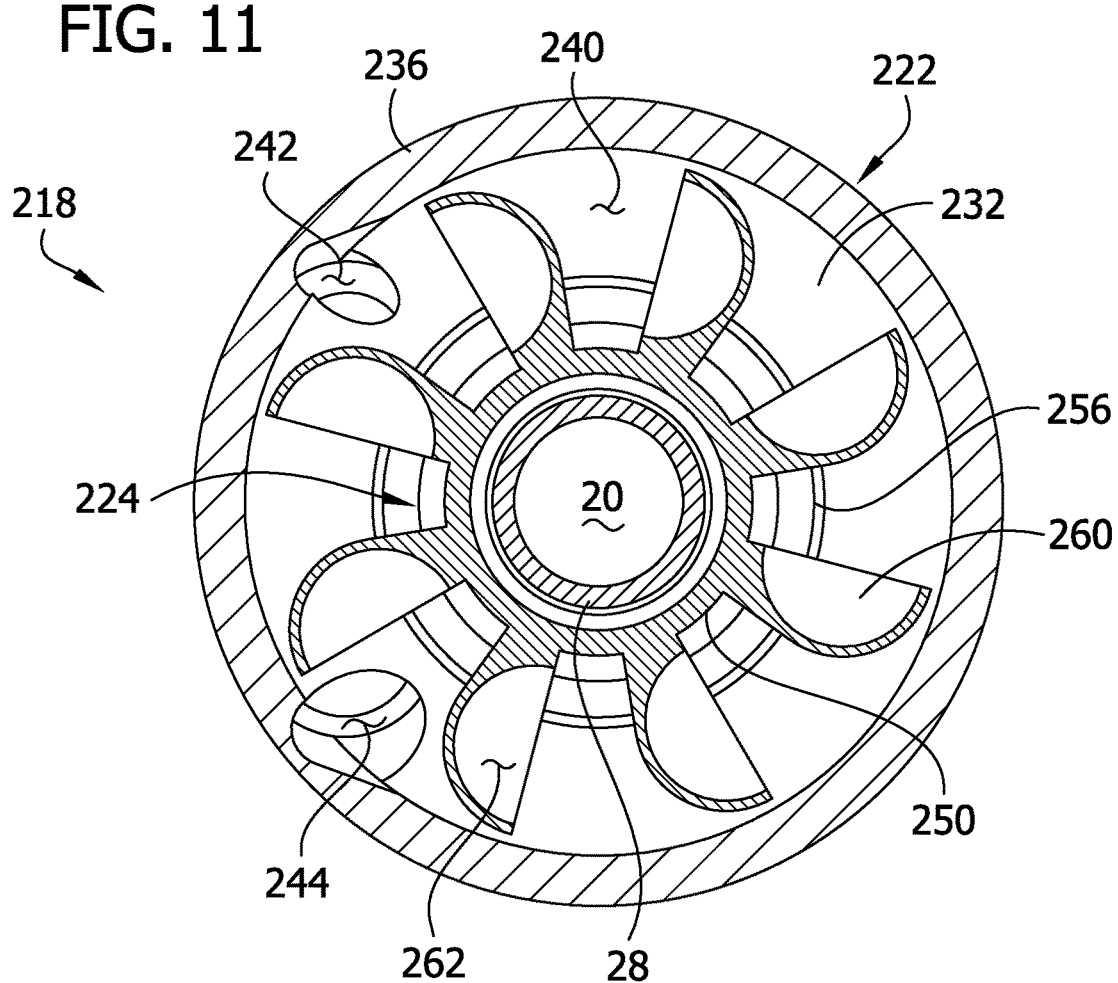
FIG. 11 is a cross section of the turbine of FIG. 7.

The housing 222 includes a distal casing 230 and a proximal cap 232. The distal casing 230 has a distal end portion 234 and an outer cylindrical wall 236 extending proximally from the distal end portion. The outer wall 236 defines a rotor chamber 240 where the rotor 224 is disposed and rotates. The proximal cap 232 is secured to the proximal end of the outer wall 236. In the illustrated embodiment, the proximal cap 232 is size and shaped to be inserted into outer wall 236 from the proximal end thereof. The cap 232 defines an inlet passageway 242 and an outlet passageway 244 that are in fluid communication with the rotor chamber 240. As shown in FIG. 11, the inlet and outlet passageways 242, 244 are on the same side of the cap 232 but spaced apart. In other words, the inlet and outlet passageways 242, 244 are disposed approximately 1.6 radians (90°) apart. The inlet passageway 242 is fluidly connected to the supply fluid passageway 51 of the supply line 52 and delivers the propellant into the rotor chamber 240. The outlet passageway 244 is fluidly connected to the return fluid passageway 56 of the return line 54 and carries the propellant from the rotor chamber 240. In one embodiment, the distal end portions of supply and return lines 52, 54 are disposed in at least a portion of the inlet and outlet passageways 242, 244, respectively, and secured to the cap 232. As shown in FIG. 11, the distal end portion of the inlet passageway 242 is configured to direct the propellant in a direction that is at least partially about the drive axis DA. Similarly, the distal end portion of the inlet passageway 244 is configured to receive the propellant in a direction that is at least partially about the drive axis DA. In this manner, the inlet and outlet passageways 242, 244 help facilitate the rotation (clockwise rotation as shown in FIG. 11) of the rotor 124 as the propellant flows through the rotor chamber 240, as described in more detail below.

The rotor 224 is disposed in the rotor chamber 240 and configured to rotate therein. The rotor 224 includes a cylindrical output shaft 250 extending distally through the rotor chamber 140 from the proximal cap 232 to the distal end portion 234 of the casing 230. The output shaft 250 is aligned with the drive axis DA and defines a portion of the guidewire lumen 20 (e.g., the output shaft has a bore there-through). A proximal end portion of the output shaft 250 is rotatably disposed in (e.g., support by) the proximal cap 232. The proximal cap 232 defines a cylindrical cavity 252 aligned with the drive axis DA that extends proximally from a distal end of the cap. The proximal end portion of the output shaft 250 is disposed in the cavity 252 such that the output shaft can rotate therein. A distal end portion of the output shaft 250 is rotatably disposed in (e.g., support by) the distal end portion 234 of the casing 230. The distal end portion 234 of the casing 230 defines an opening (aligned with the drive axis DA) through which the distal end portion of the output shaft 250 extends distally through. A pair of jewel bearings 254 and 256, respectively, are secured to the distal end portion 234 of the casing 230 and the cap 232, respectively. In particular, one jewel bearing 254 is disposed in the opening defined by the distal end portion 234 of the casing 230 and the other jewel bearing 256 is disposed in the cavity 252 (e.g., the casing and cap hold the bearings in place). The jewel bearings 254, 256 are received around the proximal and distal end portions, respectively, of the output shaft 250 and facilitate rotation of the output shaft in the housing 222. The jewel bearings 254, 256 can be made from bronze. However, other materials are also envisioned. For example, the bearings can also be made from zirconia.

Figure 9:
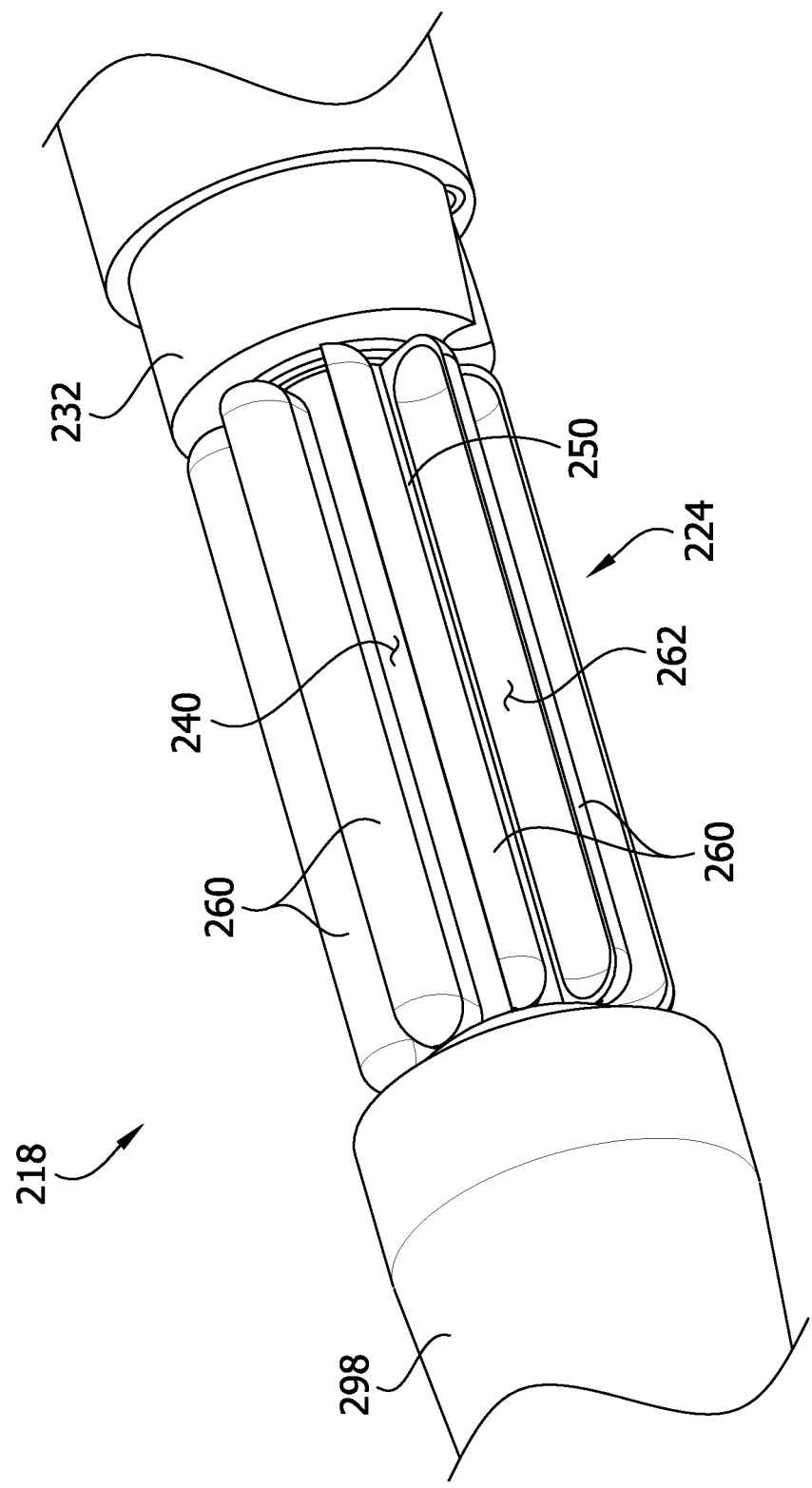
FIG. 9 is a perspective of the turbine of FIG. 7, with an outer housing removed to show internal components.
Figure 10:
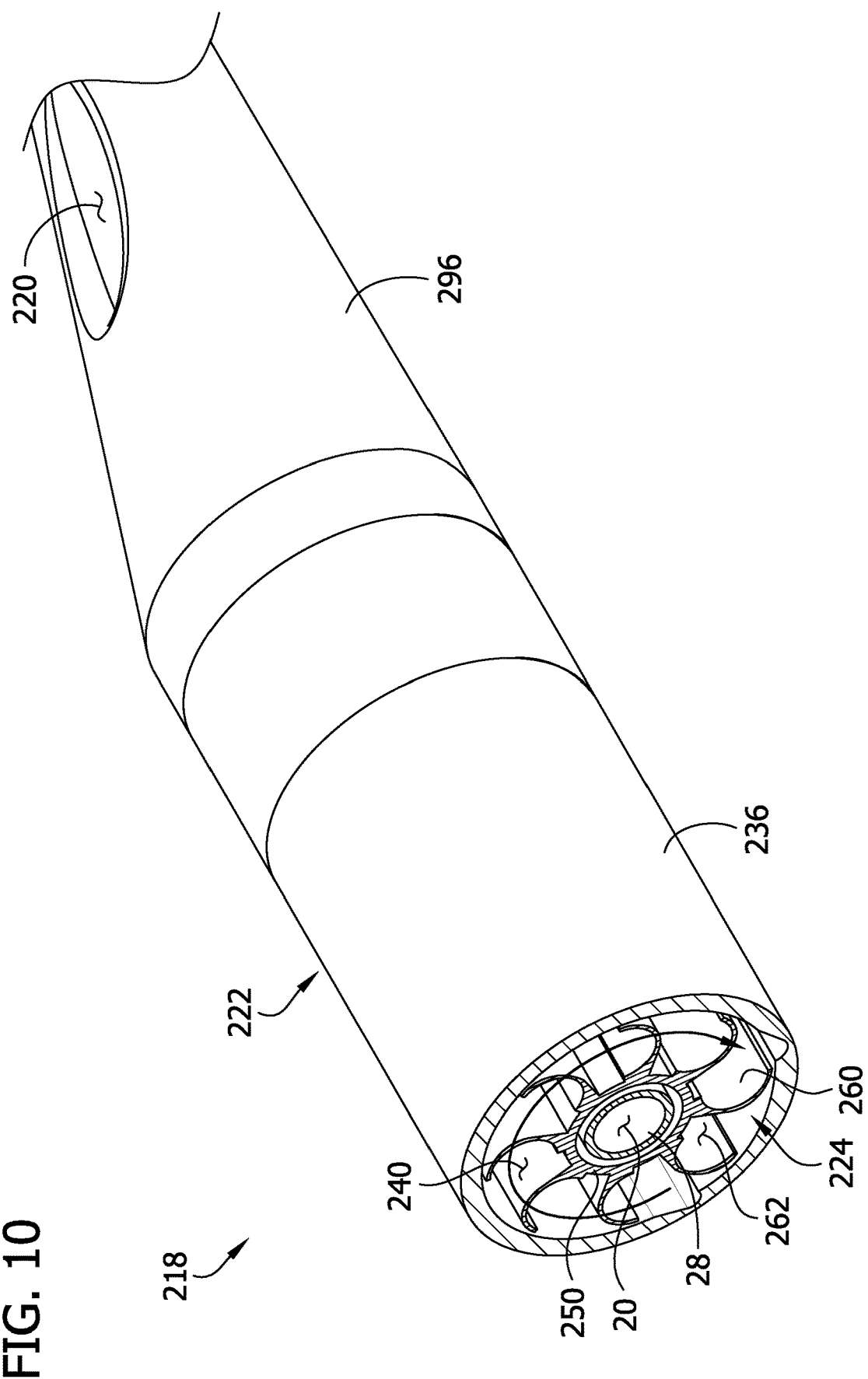
FIG. 10 is a perspective cross section of the turbine of FIG. 7.

The rotor 24 includes a plurality of circumferentially spaced apart blades 260 secured to the intermediate portion of the output shaft 250. Each blade 260 extends longitudinally along the output shaft 250 and extends radially outward (e.g., away from the drive axis DA) therefrom into the rotor chamber 240. The inner diameter of the outer wall 236 is larger than the outer diameter of the blades 260 in order to provide the necessary clearance to allow the blades to rotate within the rotor chamber 240. In the illustrated embodiment, the rotor 224 includes eight blades 260, although the rotor 224 can have more or less blades. As shown in FIGS. 9-11, each blade 260 is curved and defines a race 262 having a generally half cylinder shape with half-hemispherical ends. Thus, as shown in FIG. 11, each blade 260 has a generally semi-circular (e.g., half-circular) cross sectional shape. The blades 260 are oriented such that the race 262 will receive propellant as the propellant flows into the rotor chamber 240 through the inlet passage 242. In the illustrated embodiment, this results in the race 262 being on the counter-clockwise side of the blade 260, with the clockwise side being generally curved to reduce friction as the blade rotates in a clockwise direction. Blades 260 of other shapes are within the scope of the present disclosure. In one embodiment, the rotor 224 is integrally formed as a one piece component.

Figure 13:
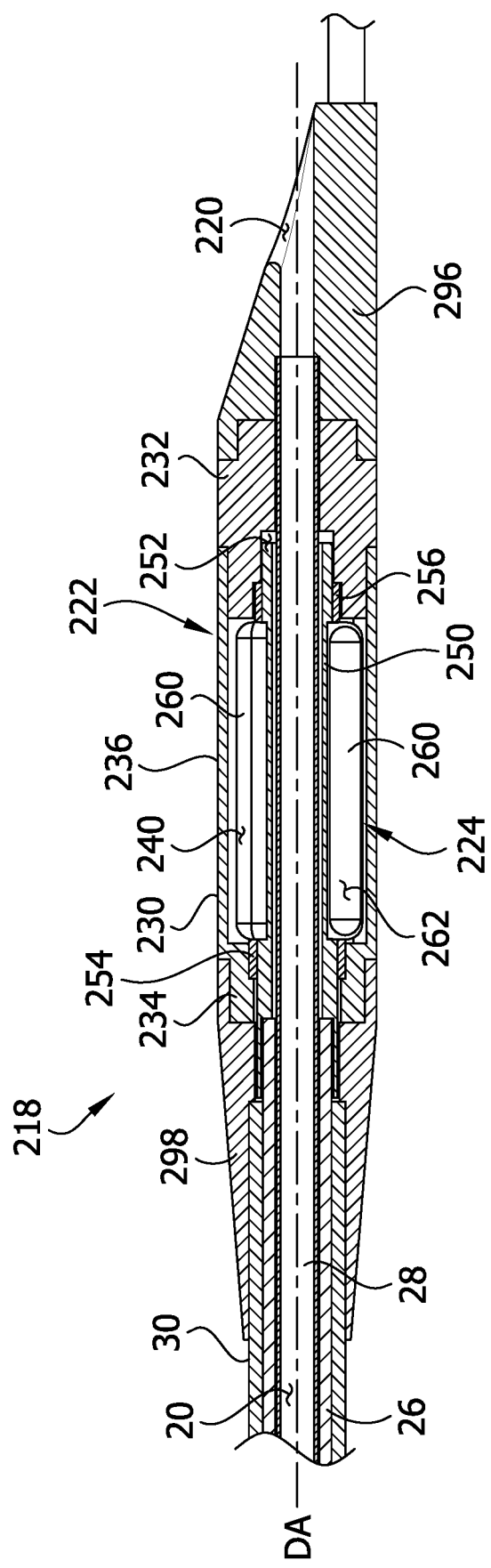
FIG. 13 is a longitudinal section of the turbine of FIG. 7.

The rotor 224 is operatively connected (e.g., attached) to the drive shaft 26 of the distal body portion 12a to drive rotation of the tissue removing element 24. In one embodiment, a proximal end portion of the drive shaft 26 extends along and is fixed to the driver shaft 250 by any suitable means, such as, but not limited to, an adhesive (FIG. 13). In other embodiment, the drive shaft 26 may be mechanically fastened to the output shaft 250. In one embodiment, the distal end portion of the output shaft 250 includes a receptacle (not shown) that receives the distal end portion of the drive shaft 26. The distal end portion of the drive shaft 26 is fixed within the receptacle to attach the drive shaft to the output shaft 250.

In the illustrated embodiment, the housing 222 of the turbine 218 also includes flexible proximal and distal end portions 296 and 298, respectively, which are secured to and extend proximally and distally, respectively, from the proximal end of the cap 232 and distal end of the distal end portion 234 to provide a strain relief function for the turbine 218 by alleviating tension applied to the turbine as the catheter 10 is bent (e.g., maneuvered) during use. In addition, the flexible proximal portion 296 defines a guidewire port 220 and a portion of the guidewire lumen 20. The guidewire port 220 enables the turbine 218 to have the rapid exchange features discussed above. The cap 232 also defines a portion of the guidewire lumen 20, specifically, the portion extending between the output shaft 250 and the flexible proximal portion 296. The proximal body portion 12b is connected to the flexible proximal portion 296 and the distal body portion 12a is connected to the flexible distal portion 298. In particular, the supply and return lines 52, 54 extend distally through the flexible proximal portion 296 to the proximal cap 232. Similarly, the sheath 30, drive shaft 26 and inner liner 28 extend proximally through the flexible distal portion 298 to the casing 230. In other words, both flexible proximal and distal portions 296, 298 define cavities sized and shaped to receive the proximal end portion of the distal body portion 12a and the distal end portion of the proximal body portion 12b. As shown in FIG. 13, the sheath 30 extends proximally into the flexible distal portion 298 and is secured therein (FIG. 13), the drive shaft 26 extends proximally through the flexible distal portion to the output shaft 250 and the inner liner 28 extends proximally through the flexible distal portion, the output shaft, the cap 232 and into the flexible proximal portion 296 and is secured to the flexible proximal portion. Preferably, the flexible proximal and distal portions 296, 298 taper inward at they extend proximally and distally, respectively, from the casing 230 and cap 232. The maximum outer diameters of the casing 230, cap 232, and flexible proximal and distal portions 296, 298 are preferably the same so that the turbine 218 has a smooth exterior surface. The distal casing 230, proximal cap 232 and the rotor 224 may be formed from polyether ether ketone (PEEK).

Figure 12:
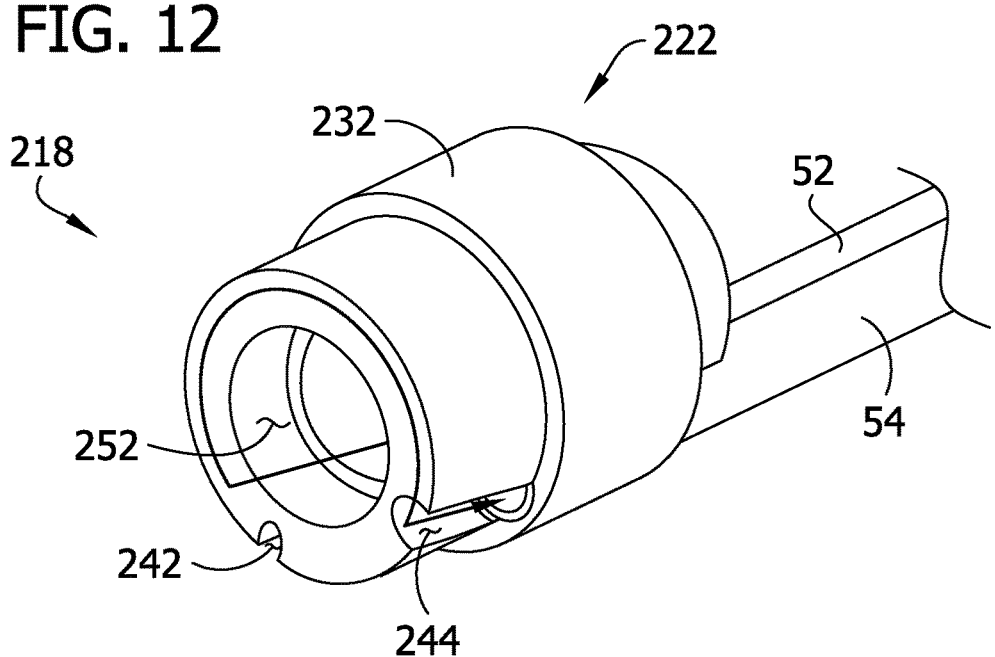
FIG. 12 is an enlarged perspective of a proximal end of the turbine of FIG. 7.

In operation, turbine 218 operates in the catheter 10 in the same manner as the turbine 118, the main difference being how the pressurized propellant flows through the turbine 218. When the practitioner operates the actuator 42 to open and set the position of the needle valve 48, the pressurized propellant flows from the source of pressurized propellant through the supply line 52 and into the rotor chamber 240 of the turbine 218. Specifically, the inlet passageway 242 directs the pressurized propellant into the rotor chamber 240 in a direction that is angled (e.g., not parallel to the drive axis DA) such that the pressurized propellant will contact the blades 260 (specifically, enter the race 262) and rotate the rotor 224 in a clockwise direction (FIG. 10). It is understood, the turbine 218 could be configured such that the rotor 224 rotates in the counter-clockwise direction. As the propellant moves through the rotor chamber 240, the propellant contacts the blades 260 which rotates the rotor 224. As the rotor 224 rotates, additional blades 260 will pass by the inlet passageway 242 and be contacted by the pressurized propellant, further rotating (e.g., continuously rotating) the rotor. The propellant flows clockwise around the output shaft 250 approximately 4.7 radians (270°) until the propellant reaches the outlet passageway 244 (FIGS. 10 and 12). The propellant then moves through the outlet passageway 244 and into the return line 54 toward the exhaust 58, where the propellant is vented into the surrounding atmosphere. It is understood that the turbine 218 can be used with an exhaust 58 that imparts a vacuum on the turbine.

Modifications and variations of the disclosed embodiments are possible without departing from the scope of the invention defined in the appended claims. For example, where specific dimensions are given, it will be understood that they are exemplary only and other dimensions are possible.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue in a body lumen, the tissue-removing catheter comprising:
    an elongate body having an axis and proximal and distal end portions spaced apart from one another along the axis, the elongate body being sized and shaped to be received in the body lumen;
    a turbine fixed to the elongate body and disposed at an intermediate position between the proximal and distal end portions of the elongate body; and
    a rotatable tissue-removing element at the distal end portion of the elongate body and operatively coupled to the turbine such that the turbine imparts rotation of the tissue-removing element, an entirety of the turbine being located proximally of the rotatable tissue-removing element and a flexible portion of the elongate body extending between the turbine and the rotatable tissue-removing element, the tissue-removing element being configured to remove the tissue from the body lumen as the tissue-removing element is rotated by the turbine.

2. A tissue-removing catheter as set forth in claim 1, further comprising a guidewire lumen extending through the elongate body from a distal end of the elongate body to the turbine, the guidewire lumen being configured to receive a guidewire such that the elongate body can move proximally and distally along the guidewire.

3. A tissue-removing catheter as set forth in claim 2, wherein the turbine defines a guidewire port for receiving the guidewire, the guidewire port defining the proximal end of the guidewire lumen.

4. A tissue-removing catheter as set forth in claim 1, wherein the turbine includes a rotor and a stator, the rotor configured to rotate about a drive axis of the turbine, the drive axis being coaxial with the axis of the elongate body.

5. A tissue-removing catheter as set forth in claim 4, wherein the rotor defines a portion of the guidewire lumen.

6. A tissue-removing catheter as set forth in claim 4, wherein the rotor is disposed in a rotor chamber defined by the stator and is configured to rotate therein.

7. A tissue-removing catheter as set forth in claim 6, wherein the rotor includes at least one impeller.

8. A tissue-removing catheter as set forth in claim 6, wherein the rotor includes at least one blade extending longitudinally along the rotor.

9. A tissue-removing catheter as set forth in claim 6, further comprising a handle mounted to the proximal end portion of the elongate body and operable to deliver a flow of propellant to the turbine to rotate the rotor.

10. A tissue-removing catheter as set forth in claim 9, wherein the propellant flows proximally and distally within the rotor chamber when the flow of propellant is delivered to the turbine.

11. A tissue-removing catheter as set forth in claim 9, wherein the propellant flows circumferentially around the rotor in the rotor chamber when the flow of propellant is delivered to the turbine.

12. A tissue removing catheter as set forth in claim 9, wherein the elongate body further includes a supply line extending between the handle and the turbine and configured to deliver the flow of propellant to the turbine from the handle.

13. A tissue removing catheter as set forth in claim 12, further comprising an exhaust fluidly connected to the turbine and configured to vent the propellant into the atmosphere surrounding the exhaust after at least a portion of the propellant flows through the turbine.

14. A tissue removing catheter as set forth in claim 13, wherein the elongate body further includes a return line extending between the turbine and the exhaust and configured to transport the propellant to the exhaust after the propellant flows through the turbine.

15. A tissue removing catheter as set forth in claim 14, wherein the exhaust imparts a vacuum on the turbine to facilitate the movement of the propellant through the turbine.

16. A tissue removing catheter as set forth in claim 15, further comprising an exhaust supply line extending between the handle and a nozzle and configured to divert a portion of the propellant from the turbine and directly into the exhaust.

17. A tissue removing catheter as set forth in claim 16, wherein the exhaust constricts the flow of propellant from the exhaust supply line before the flows of the propellant from the return line and exhaust supply line mix to impart the vacuum on the turbine.

18. A tissue removing catheter as set forth in claim 9, wherein the handle further includes a canister configured to hold the propellant under pressure.

19. A tissue removing catheter as set forth in claim 9, wherein the handle further includes a selectively operable needle valve to control the flow of the propellant to the turbine and a selectively operable pressure regulator to control the pressure of the propellant.

20. A method of removing tissue in a body lumen, the method comprising:
    advancing an elongate body through the body lumen to position a distal end portion of the elongate body adjacent the tissue and a proximal end portion of the elongate body outside of the body lumen;
    using an actuator outside the body lumen to deliver a flow of propellant to a turbine mounted at an intermediate position between the proximal and distal end portions of the elongate body to rotate a tissue-removing element about a longitudinal axis of the elongate body to remove the tissue, whereby an entirety of the turbine is located proximally of the tissue-removing element and a flexible portion of the elongate body extending between the turbine and the rotatable tissue-removing element; and
    using the actuator outside the body lumen to control the flow of the propellant to the turbine to control the rotational speed and/or torque of the tissue-removing element.

21. A tissue-removing catheter for removing tissue in a body lumen, the tissue-removing catheter comprising:
    an elongate body having an axis and proximal and distal end portions spaced apart from one another along the axis, the elongate body being sized and shaped to be received in the body lumen;
    a turbine fixed to the elongate body and disposed at an intermediate position between the proximal and distal end portions of the elongate body, wherein the turbine includes a rotor and a stator, the rotor configured to rotate about a drive axis of the turbine, the drive axis being coaxial with the axis of the elongate body;
    a rotatable tissue-removing element at the distal end portion of the elongate body and operatively coupled to the turbine such that the turbine imparts rotation of the tissue-removing element, the tissue-removing element being configured to remove the tissue from the body lumen as the tissue-removing element is rotated by the turbine;

a handle mounted to the proximal end portion of the elongate body and operable to deliver a flow of propellant to the turbine to rotate the rotor;

an exhaust fluidly connected to the turbine and configured to vent the propellant into the atmosphere surrounding the exhaust after at least a portion of the propellant flows through the turbine, wherein the elongate body further includes a return line extending between the turbine and the exhaust and configured to transport the propellant to the exhaust after the propellant flows through the turbine, and wherein the exhaust imparts a vacuum on the turbine to facilitate the movement of the propellant through the turbine; and an exhaust supply line extending between the handle and a nozzle and configured to divert a portion of the propellant from the turbine and directly into the exhaust, wherein the exhaust constricts the flow of propellant from the exhaust supply line before the flows of the propellant from the return line and exhaust supply line mix to impart the vacuum on the turbine.

* * * * *